United States Patent
Arsenault et al.

(10) Patent No.: US 10,022,258 B2
(45) Date of Patent: Jul. 17, 2018

(54) BACK SUPPORT GARMENT APPARATUS

(71) Applicants: James Arsenault, East Williston, NY (US); Paul Iskyan, Manhasset, NY (US); Vijay Vad, New York, NY (US)

(72) Inventors: James Arsenault, East Williston, NY (US); Paul Iskyan, Manhasset, NY (US); Vijay Vad, New York, NY (US)

(73) Assignee: Golf Jox, Inc., East Orange, NJ (US)

( * ) Notice: Subject to any disclaimer, the term of this patent is extended or adjusted under 35 U.S.C. 154(b) by 608 days.

(21) Appl. No.: 14/341,608

(22) Filed: Jul. 25, 2014

(65) Prior Publication Data

US 2014/0378880 A1 Dec. 25, 2014

Related U.S. Application Data

(63) Continuation of application No. PCT/US2012/022882, filed on Jan. 27, 2012, which
(Continued)

(51) Int. Cl.
  *A61F 5/02* (2006.01)
  *A61F 7/00* (2006.01)

(52) U.S. Cl.
  CPC .............. *A61F 5/028* (2013.01); *A61F 7/00* (2013.01); *A61F 2007/0024* (2013.01); *A61F 2210/0076* (2013.01)

(58) Field of Classification Search
  CPC .............. A61B 5/6804; A61B 5/04085; A61B 5/02055; A61B 5/0245; A61B 5/0002;
(Continued)

(56) References Cited

U.S. PATENT DOCUMENTS

| 2,249,198 A | 7/1941 | Carter |
| 2,553,353 A | 5/1951 | Binder et al. |

(Continued)

FOREIGN PATENT DOCUMENTS

| CN | 201219940 Y | 4/2009 |
| EP | 0636325 B1 | 3/1999 |

(Continued)

OTHER PUBLICATIONS

The Saunders Group, Inc., S'port All Back Support, 2006.
(Continued)

*Primary Examiner* — Ophelia A Hawthorne
(74) *Attorney, Agent, or Firm* — Tiajoloff & Kelly LLP

(57) ABSTRACT

A back support system has a belt portion that is configured to provide back and abdominal support encircling a wearer's waist, a compression pants portion and a hot or cold pack providing therapy to a wearer's lumbosacral region. The belt portion has left and right portions and a rear portion that extends upwardly from a cutout of the rear portion of the compression pants and it is attached fixedly to it. The rear portion of the belt portion has a pack support structure for receiving a hot or cold pack so as to maintain hot or cold therapy on the wearer's back. A front core support structure provides abdominal support that in combination with the back support supports the entire core of the wearer's body. The garment can be changed to an immobilizing brace device by inserting optional rigid inserts.

32 Claims, 18 Drawing Sheets

Related U.S. Application Data is a continuation-in-part of application No. 12/983,831, filed on Jan. 3, 2011, now Pat. No. 8,291,519, which is a continuation of application No. 12/079,161, filed on Mar. 25, 2008, now Pat. No. 7,882,574.

(58) Field of Classification Search
CPC ... A61B 5/0022; A61B 5/1135; A61B 5/0006; A61B 2562/12; A61B 5/0416; A61B 5/6807; A61B 5/6831; A61B 17/1322; A61F 5/028; A61F 2007/0001; A61F 2007/0022; A61F 2007/0023; A61F 2007/0024; A61F 2007/0025; A61F 2007/0026; A61F 2007/0027; A61F 2007/0231; A61F 2007/0238; A61F 7/02; A41D 13/00; A41D 13/0012; A41D 13/0015; A41D 13/0051; A41D 13/015; A41D 13/0506; A41D 13/0525; A41D 13/0531; A41D 13/0058; A41D 13/0575; A41D 1/06; A41D 1/067; A41D 1/08; A41D 1/20; A41D 2400/10; A41D 2400/32; A41D 2400/38; A41D 2400/60; A41D 2400/62; A41C 1/02; A41C 1/08; A41C 1/10; A41B 9/00; A41B 9/004; A41B 9/02; A41B 9/04; A41B 9/08; Y10S 2/912; Y10S 2/919
USPC ...... 602/19, 74–75, 14, 60, 61, 67; 2/24, 44, 2/221, 223, 227, 228, 235, 236, 237, 238, 2/267, 310, 311, 312, 321, 338, 400, 403, 2/404, 465, 467, 466; 128/96.1, 98.1, 128/99.1, 100.1, 101.1, 106.1, 876; 450/94–104

See application file for complete search history.

(56) References Cited

U.S. PATENT DOCUMENTS

| | | | |
|---|---|---|---|
| 4,108,149 A * | 8/1978 | Castiglia | A41C 1/10 450/155 |
| 4,676,247 A | 6/1987 | Van Cleve | |
| 4,836,194 A * | 6/1989 | Sebastian | A61F 5/028 128/DIG. 20 |
| 4,972,832 A | 11/1990 | Trapini et al. | |
| 5,038,779 A | 8/1991 | Barry et al. | |
| 5,157,790 A | 10/1992 | Aldridge | |
| 5,179,942 A | 1/1993 | Drulias et al. | |
| 5,188,585 A * | 2/1993 | Peters | A61F 5/028 128/100.1 |
| 5,205,815 A * | 4/1993 | Saunders | A41D 13/0525 450/150 |
| 5,351,340 A | 10/1994 | Aldridge | |
| 5,398,667 A | 3/1995 | Witt | |
| 5,399,150 A * | 3/1995 | Saunders | A41D 13/0525 128/100.1 |
| 5,403,271 A * | 4/1995 | Saunders | A41D 13/015 128/876 |
| 5,471,680 A | 12/1995 | Vesterinen | |
| 5,484,366 A | 1/1996 | Wilkinson | |
| 5,533,961 A | 7/1996 | Iwata | |
| 5,536,246 A * | 7/1996 | Saunders | A61F 5/028 128/101.1 |
| 5,605,144 A | 2/1997 | Simmons et al. | |
| 5,611,084 A | 3/1997 | Garry et al. | |
| 5,665,057 A | 7/1997 | Murphy | |
| 5,716,388 A | 2/1998 | Petelle | |
| 5,722,940 A | 3/1998 | Gaylord | |
| 5,732,940 A | 3/1998 | Gaylord | |
| 5,928,275 A | 7/1999 | Yates et al. | |
| 5,984,885 A | 11/1999 | Gaylord | |
| 6,006,363 A | 12/1999 | Karlin | |
| 6,099,490 A * | 8/2000 | Turtzo | A61F 5/028 2/311 |
| 6,108,819 A | 8/2000 | DeBaene et al. | |
| 6,119,275 A | 9/2000 | Goyal | |
| 6,205,591 B1 | 3/2001 | Wheeler et al. | |
| 6,367,086 B1 | 4/2002 | Woodard | |
| 6,585,673 B1 | 7/2003 | Bass | |
| 6,656,210 B1 * | 12/2003 | Plewes | A61F 7/02 128/DIG. 15 |
| 7,882,574 B2 | 2/2011 | Arsenault et al. | |
| 8,291,519 B2 | 10/2012 | Arsenault et al. | |
| 2005/0090882 A1 | 4/2005 | Wei | |
| 2005/0229295 A1* | 10/2005 | Chun | A41C 1/003 2/467 |
| 2005/0268379 A1 | 12/2005 | MacGeorge | |
| 2007/0077860 A1* | 4/2007 | Brooks | A41B 9/04 450/155 |
| 2007/0094775 A1* | 5/2007 | Chun | A41C 1/08 2/255 |
| 2008/0171955 A1* | 7/2008 | Jaccard | A61F 5/028 602/19 |
| 2009/0254017 A1* | 10/2009 | Dumpson | A41C 1/02 602/67 |
| 2011/0172577 A1 | 7/2011 | Arsenault et al. | |
| 2013/0019371 A1* | 1/2013 | Abeysekera | A41D 1/08 2/69 |

FOREIGN PATENT DOCUMENTS

| | | |
|---|---|---|
| GB | 2 259 848 B | 12/1995 |
| JP | 2004229783 A | 8/2004 |
| WO | 2013112175 A1 | 8/2013 |

OTHER PUBLICATIONS

The Saunders Group, Inc., S'port Max Back Support, 2006.
Espacenet English Language Abstract for JP2004-229783, Aug. 19, 2004.
Espacenet. English Language Translation of CN201219940, Wegqing Wang, Apr. 15, 2009.

* cited by examiner

BACK SUPPORT GARMENT APPARATUS

CROSS-REFERENCE TO RELATED APPLICATIONS

The present invention is a continuation of international patent application serial no. PCT/US2012/022882, filed Jan. 27, 2012 and designating the United States of America, published as WO 2013/112175 A1 on Aug. 1, 2013, which is a continuation-in-part of U.S. patent application Ser. No. 12/983,831, filed on Jan. 3, 2011, and published as patent application publication US 2011/0172577 A1 on Jul. 14, 2011, and also claims priority of U.S. patent application Ser. No. 12/079,161, filed on Mar. 25, 2008, now issued as U.S. Pat. No. 7.882,574, all three of which applications are herein incorporated in their entirety by reference.

FIELD OF THE INVENTION

The present invention relates to bank support garments, and more particularly to a one-piece support belt and compression pants apparatus.

BACKGROUND OF THE INVENTION

Millions of Americans suffer from back injuries and back pain, which can easily be aggravated by participation in athletic, physical, and even everyday activities. The lower back, or lumbar region, supports the weight of the upper body and is the most common site of back injuries. Treatment for back injuries often involves restoring strength to the back and preventing recurrence of the injury.

Back patients often wear back support garments to compress and restrict movement in the lumbar spine and surrounding muscles to prevent further back strain. There are many variations of compressive back supports in the prior art. These often consist or a back support device made from a stiff fabric configured to compress the wearer's waist area.

Although several back supports exist in the prior art, most existing back support apparatuses provide compressive support only to the lumbar area, and fail to extend support to the tailbone region of the spine and its surrounding muscles, which are also vulnerable to injury. Furthermore, back supports of the prior art also do not provide adequate compressive support to a wearer's leg, buttocks, hip, pelvis and groin muscles. In addition, they do not provide for localized therapeutic heating or cooling of the lumbar region. They also do not stay in place during physical, daily or athletic activity.

SUMMARY OF THE INVENTION

It is accordingly an object of the present invention to provide a back support apparatus that does not have the drawbacks of the prior art.

An object of the present invention is to provide a one-piece apparatus that evenly distributes forces applied on the body during athletic, physical and every day activity, in particular those applied during twisting or forward bending movements, such as when swinging a golf club or skiing downhill, working, etc., over a wearer's lumbar to mid-thigh regions, while simultaneously providing therapeutic heating and cooling benefits.

In accordance with an aspect of the present invention, a pack support garment for a wearer includes a compression pants portion configured to provide support for the wearer's pelvis, legs, buttocks, hip, and groin area. A belt portion attached fixedly to and extending upwardly from the compression pants portion and has a rear portion configured to support to a lumbar and an abdominal area of the wearer. The belt portion is attached to the pants portion so as to align its rear portion with the lumbar region of the wearer.

In another embodiment of the invention, the back support garment has a pack support structure with one or more slots supporting therein one or more hot or cold packs adjacent an inner surface of the pack support structure. The belt portion is attached to the pants portion so as to align the pack support portion with a lumbar region of the wearer and to maintain temperature transferring contact between the inner surface of the belt portion adjacent the hot and cold packs and the wearer's lumbar region.

According to an aspect of the invention, the compression pants portion is shorts extending no lower than the thighs of the wearer. In another aspect of the invention, the compression pants portion extends past the wearer's knees.

In another aspect of the invention, a rear portion of the belt portion has an insert receiving structure with one or more slots supporting therein one or more inserts configured to provide further support for the wearer's back.

According to another aspect of the invention, a support garment for a wearer comprises a compression pants portion configured to provide support for the wearer's pelvis, legs, and groin area and a belt portion attached fixedly to and extending upwardly above the compression parts portion. The belt portion is configured to support a lumbar region of the wearer, and it includes a rear portion configured to overlay and support the lumbar region of the wearer. The belt portion is attached to the pants portion so as to align the rear portion with the lumbar region of the wearer.

According to another aspect of the invention, a support garment for a wearer comprises a compression pants portion configured to provide support for the wearer's pelvis, legs, and groin area and a belt portion attached fixedly to the compression pants portion and including a rear portion configured to align with, overlay and support the lumbar region of the wearer when wearing the garment. The compression pant portion supports thereon a core support structure generally over the lower abdomen of the wearer when wearing the garment. The core support structure includes at least one reinforcement structure providing support for the abdomen of the wearer.

According to still another aspect of the invention, a support garment for a wearer has compression pants configured to provide support for the wearer's pelvis, legs, and groin area, and a rear portion of a first elastic material affixed to said compression pants so as to align with a lumbar region of the wearer's spine when the wearer wears the compression pants. A pair of elastic segments of a second elastic materiel that stretches more easily than the first elastic material extend laterally from respective lateral sides of the rear portion. A pair of belt closing portions are connected to ends of the elastic segments distal to the rear portion. The compression pants support on a forward abdominal portion thereof a core support structure having reinforcement structures therein configured to support a pert of the abdomen of the wearer. The belt closing portions have co-acting securement structures by which the belt closing portions are releasably secured to each other in front of the core support portion at selectable locations so as to provide selectable amounts of compression at the rear portion and the forward abdominal portion. The rear portion has one or more vertically extending flexible reinforcement members and is configured to align with and support a lumbosacral region of the wearer centered on a midpoint between the L4 and L5 vertebrae of the wearer when the wearer is wearing the garment. The rear portion has an innermost surface facing the lumbosacral region of the wearer, and the innermost surface comprises a layer of fabric or mesh defining behind it a pouch configured to receive a hot or cold pack such that the hot or cold pack is separated from the innermost surface only by the layer of fabric or mesh. The hot or cold pack is sized to apply hot or cold treatment under compression to the lumbosacral area of the wearer. The wearer is provided with compression support of both the abdomen portion and lumbosacral area with hot or cold treatment applied to the lumbosacral area without movement thereof during activity of the wearer when wearing the garment.

Other objects and advantages of the invention herein will become apparent in the specification below.

DETAILED DESCRIPTION

Figure 1:
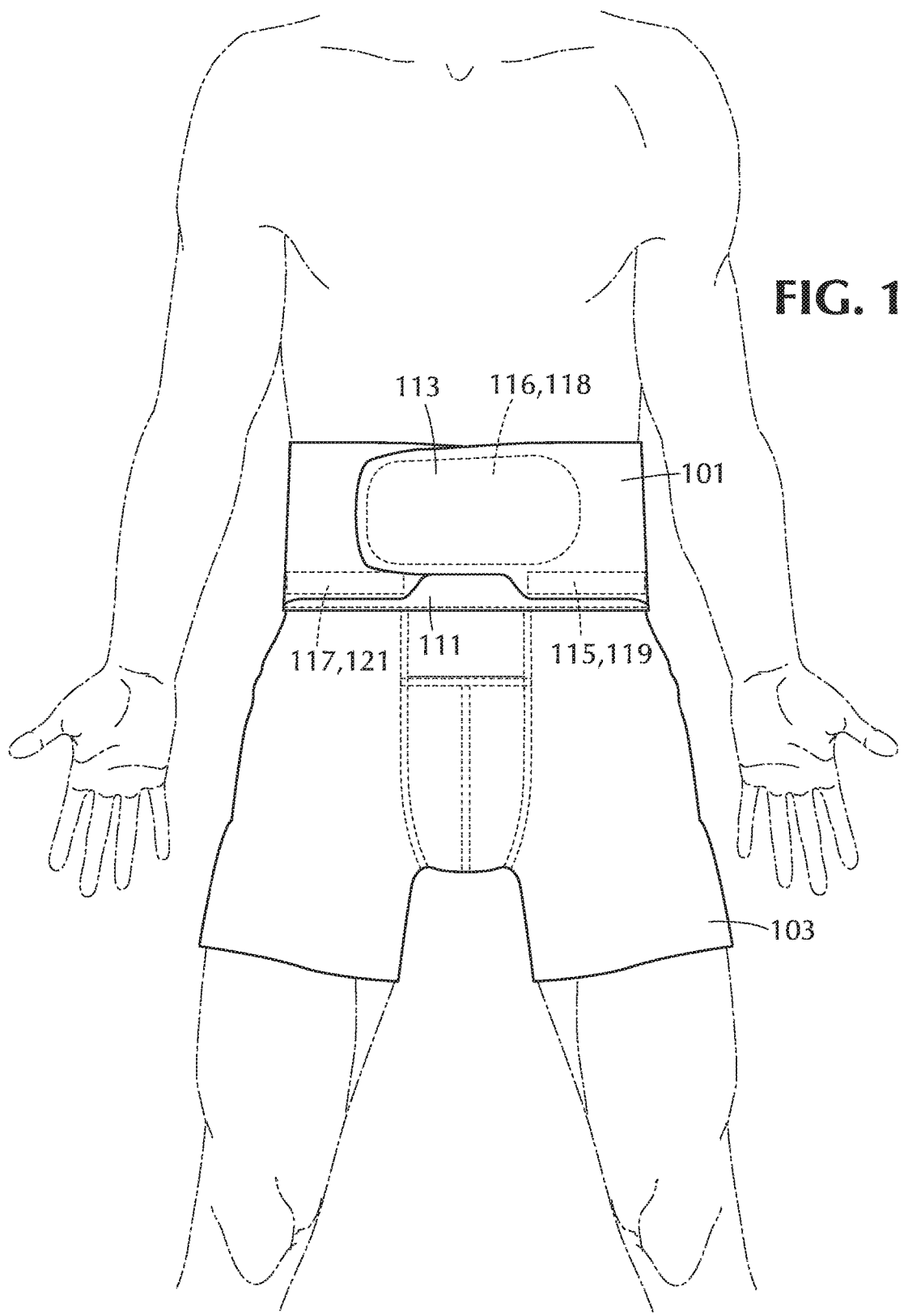
FIG. 1 is a front view of an embodiment of the support garment of the invention, as worn by a user.
Figure 2:
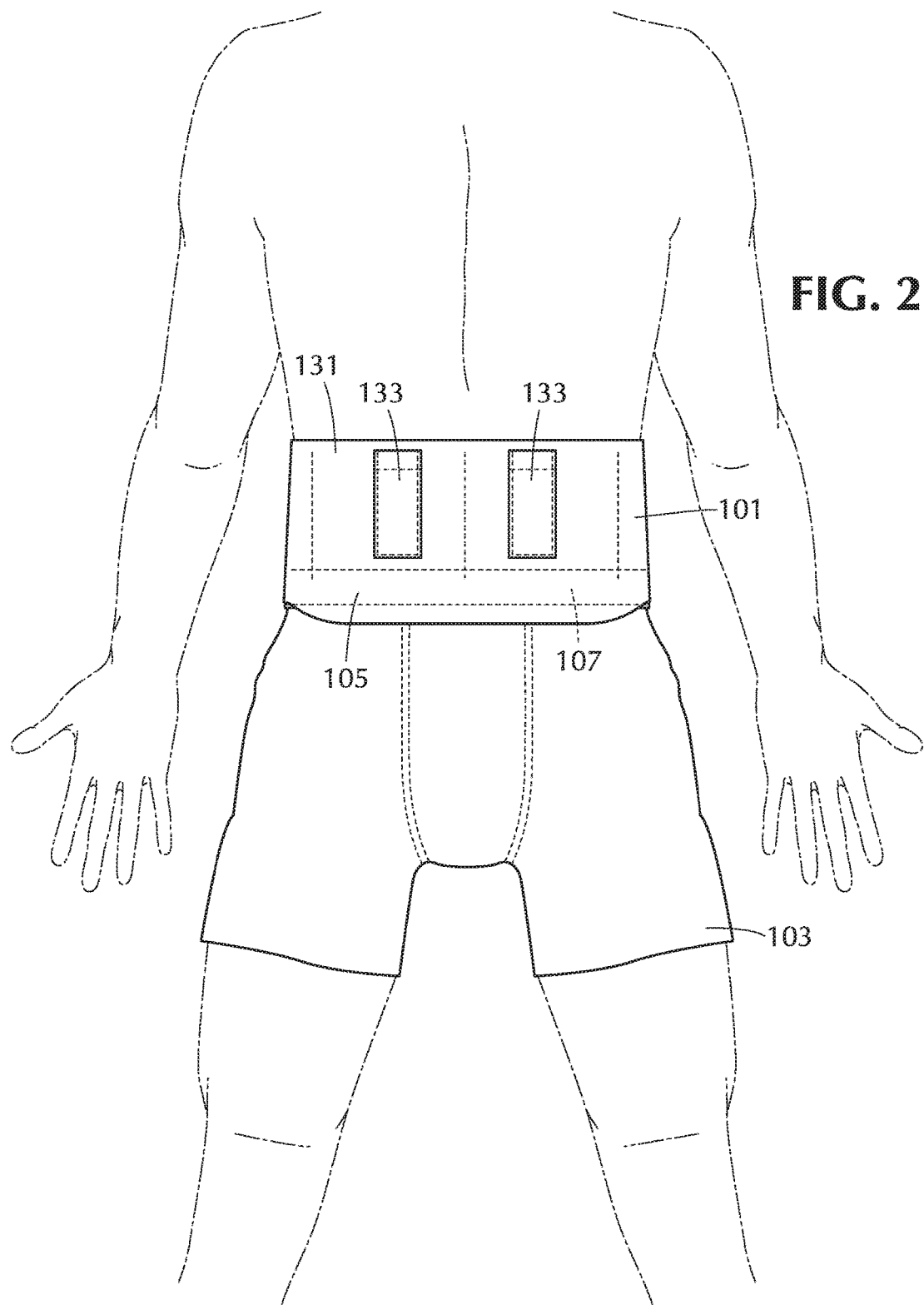
FIG. 2 is a rear view of the support garment of FIG. 1.
Figure 3:
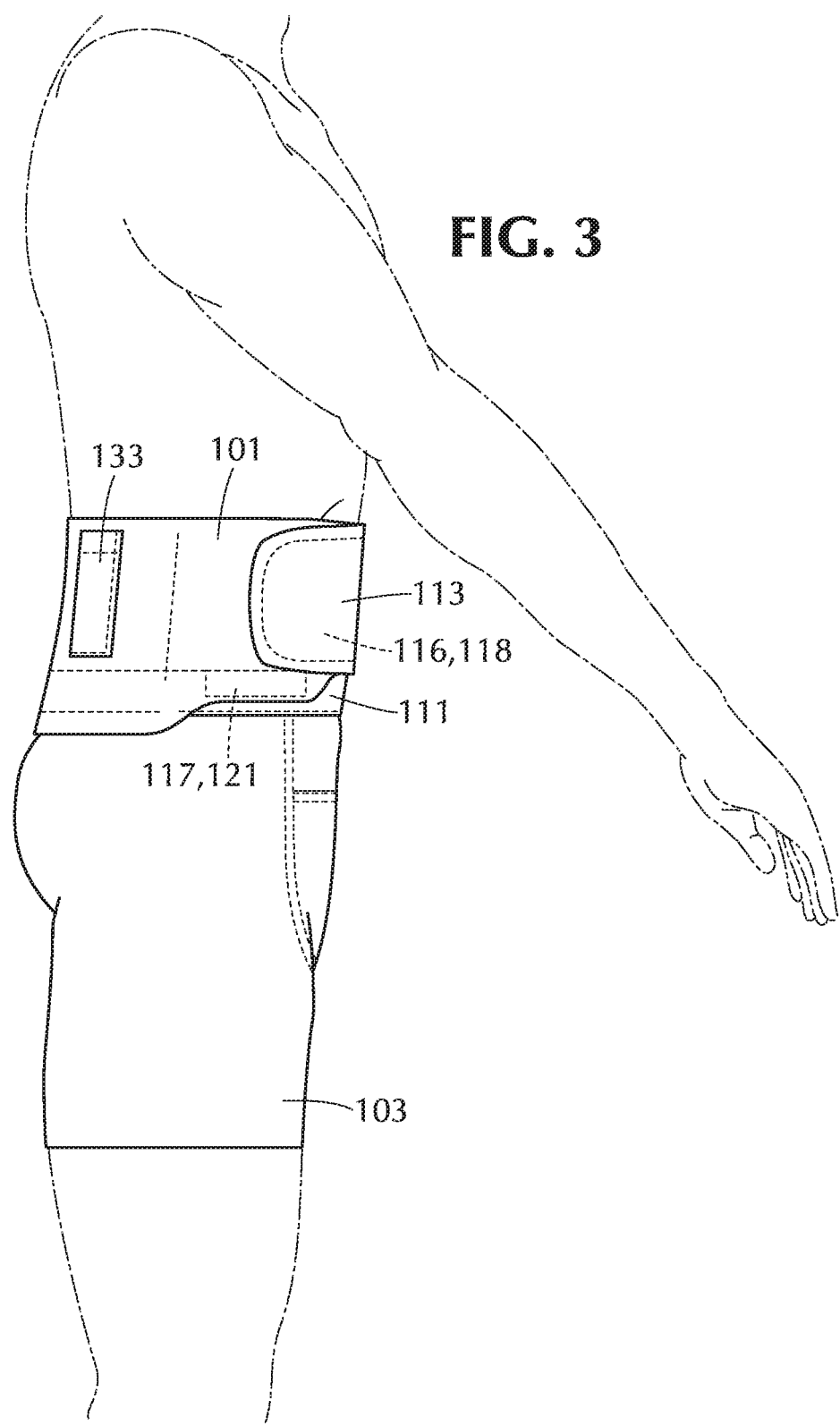
FIG. 3 is a left-hand side view of the support garment of FIGS. 1 and 2.

As best seen in FIGS. 1, 2 and 3, the present apparatus generally comprises a unitary garment having a belt portion 101 and a compression pants portion 103. Belt portion 101 encircles the waist of a wearer, and extends upwardly from the compression pants portion 103.

As shown in FIGS. 2 and 3, the rear portion 105 of the belt portion 101 is fixedly secured to a rear portion 107 of the pants portion 103, thus locating the belt of the user when wearing the pants portion 103, and preventing separation of the pants portion 103 from the belt portion 101 when the wearer moves. Securing the pants portion 103 and the belt portion 101 distributes the compressive support provided by the pants and the belt individually over the entire lumbar region extending from the wearer's waist to the wearer's tailbone area.

Figure 4:
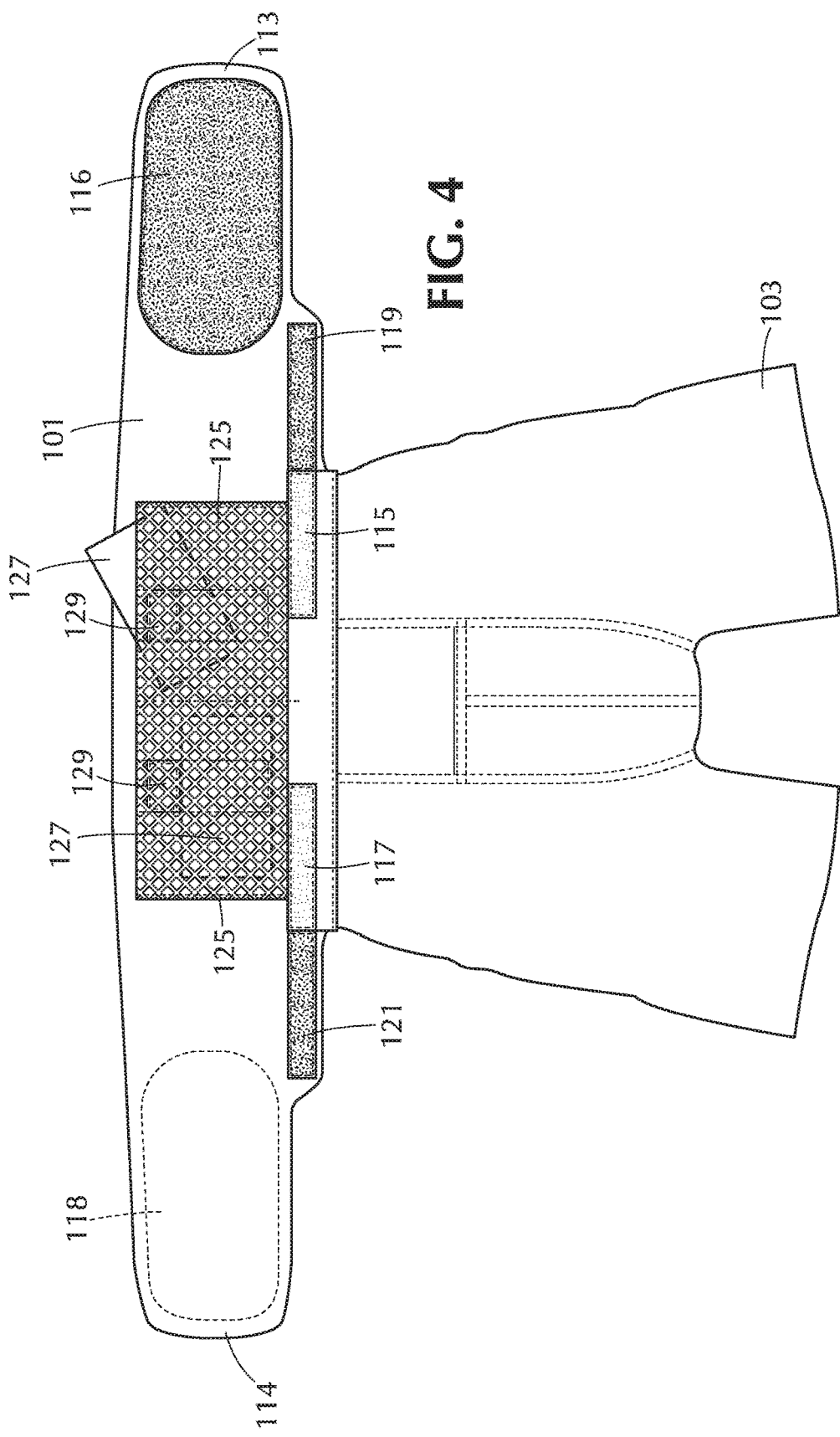
FIG. 4 is a front view of the garment of FIGS. 1-3 when not worn, showing the pack support structure having multiple slots for receiving hot or cold packs.
Figure 5:
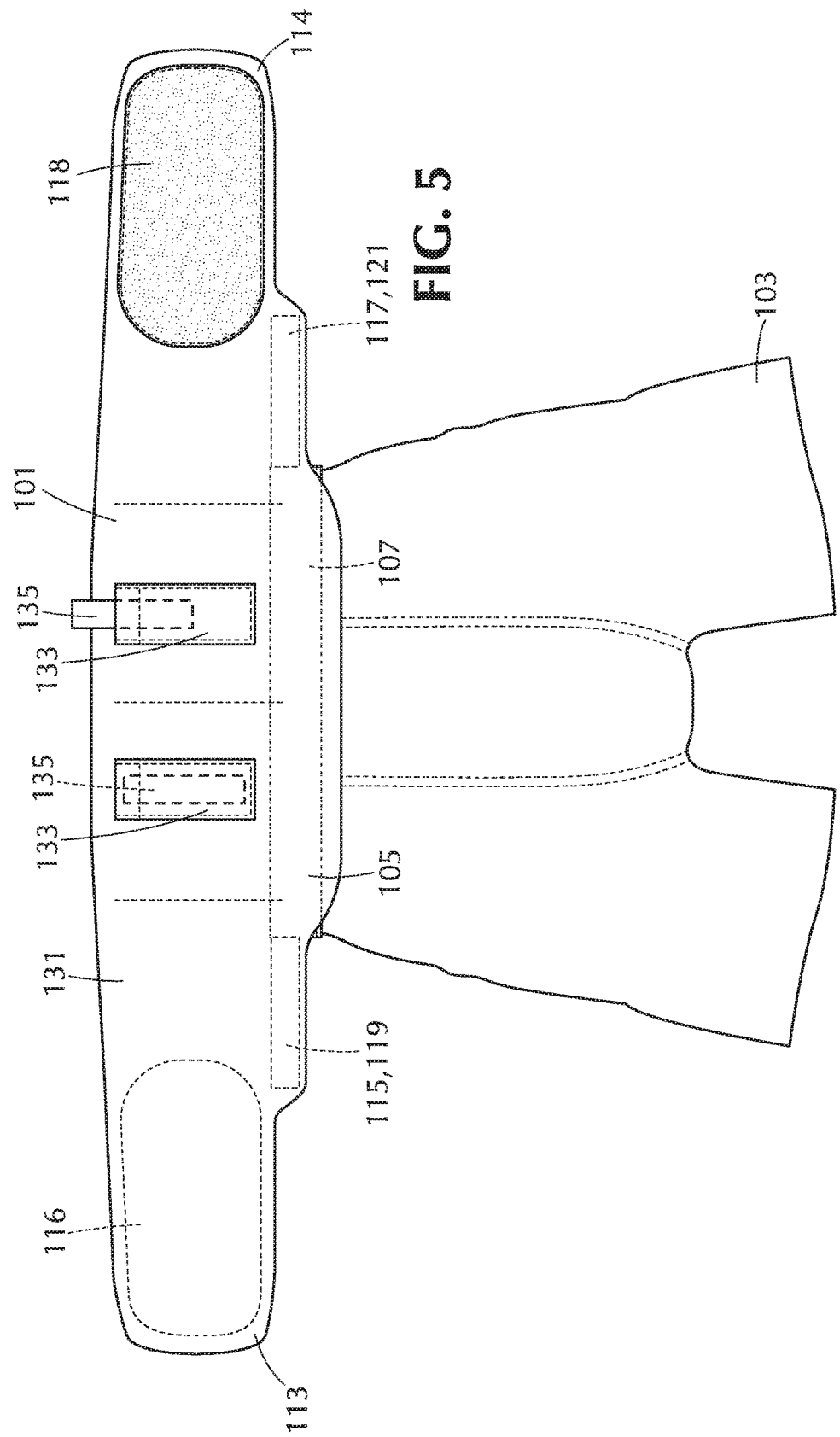
FIG. 5 is a back view of the garment as seen in FIG. 4.

Referring to FIG. 5, the rear portion 107 of the pants portion 103 and the rear portion 105 of the belt portion 101 are fixedly secured to each other, as by glue or stitching, while, as shown in FIG. 4, the forward waistband portion 111 of the pants portion 103 and the forward portion 113 of the belt portion 101 are configured so as to be releasably attachable to one another by releasable connection structures or means. These portions 111 and 113 are adjustably and releasably connected with each other so that the user can adjust a relative position of the forward waistband portion 111 of the pants portion 103 in relation to the forward portion 113 of the belt portion 101, so as to comfortably conform the garment to the wearer's body.

In the embodiment depicted in FIG. 4, the forward waistband portion 111 of the pants portion 103 has secured thereon one or more strips of a hook and loop fastening fabric strips 115 and 117, such as VELCRO™. The unsecured bottom portion of the belt portion 101 are lined with complementary strips of hook and loop fastening fabric strips 119 and 121, respectively, extending circumferentially about the waist of the user and that releasably secure the forward portion 113 of belt portion 101 to forward portion 111 of pants portion 103, by co-acting securement of fabric strips 115 and 117 with fabric strips 119 and 121.

The compression pants portion 103 is constricted from a light-weight elastic material having the requisite stiffness and elasticity to compressively support the abdominal, groin, buttock, hip, and leg, muscles of the wearer, while also being comfortable and providing ease of movement during athletic, physical or daily activity. Examples of materials which are suitable for these purposes include fabrics containing Lycra™, Spandex™, or a similar stretch material. In the preferred embodiment of the invention, the material further has moisture-wicking capabilities which further prevent chafing and allow for cooling of the covered muscles when the user is performing sweat-inducing activities.

In the preferred embodiment, the compression pants portion 103 is shorts that extend no lower than the thighs of the wearer, from the wearer's waist area to a mid or lower thigh position. This length provides compressive support to the wearer's abdominal, groin, buttocks, hip, pelvis quadriceps muscles, and is suitable for wear during most athletic, physical, or everyday activities.

The belt portion 101 is constructed from a stiff fabric to enhance stabilization and support of the lumbar region, while also allowing the wearer enough freedom of movement to engage in athletic, physical or daily activity requiring twisting or bending of the spine. Synthetic laminated of woven stretchable fabrics, such as Neoprene, manufactured by the DuPont Corporation, are desirable due to their stiffness, flexibility, and insulating properties. In the preferred embodiment of the invention, the material is a permeable or breathable fabric that also wicks perspiration away from the skin for enhanced comfort such as BREATHE-O-PRENE™, by AccuMED Technologies, Inc. The material forming the belt portion is sufficiently thin so as to make the belt invisible when worn under other garments or athletic attire. Preferably, the overall thickness of the belt is between 1 mm and 5 mm, as this provides the requisite amount of lumbar support, while maintaining the invisibility of the belt under the wearer's outer garments.

Use of the above materials is desirable for their mechanical properties, but such material may cause sticking of the wearer's outer garments to the belt. Accordingly, the outer surface of the belt is covered by a thin, smooth fabric such as Nylon so as to minimize friction between the user's outer clothing and belt during periods of contact, and to prevent bunching of the wearer's outer garments around the belt. The fabric covering the outer surface of the belt should be so thin that it has no, or minimal effect on the overall thickness of the belt.

As best seen in FIGS. 4 and 5 belt portion 101 has a first and second ends 113 and 114, that are each configured so as to be releasably attachable to each other, allowing the wearer to fasten the belt portion 101 tightly around the wearer's waist in a range of possible waist sizes, so as to wear the belt snugly as depicted in FIGS. 1, 2 and 3. The first end 113 of the belt portion 101 has secured thereon a patch 116 of hook and loop type fastening fabric, and the second end 114 of the belt portion 101 is lined with a complementary co-acting patch 118 of hook and loop type fastening fabric. The patches 116 and 118 are large enough about the waist of the wearer, and configured to be releasably seared to each other in a variety of waist size positions and with some varying angulation, if desired. Alternatively, the entire inner surface 123 of the belt can be lined with the loop material so as to co-act with a patch of hook fabric secured onto the second end 114 of the belt. Other types of fastening mechanisms, such as a buckle or lace-up configuration having openings in it may also be used to adjustably secure the belt portion 101 around the waist of the user.

As shown in FIG. 4, the inner surface 123 of the belt portion 101 includes two pack support structures 125 with one or more slots therein configured to receive therapeutic hot or cold packs 127. The pack support structures 125, which are secured to the inner surface 123 of the belt portion 101 by glue or stitching, are positioned so as to maintain temperature transferring contact between the inner fabric of the support structures 125 adjacent the inserted therapeutic packs 127 and the lumbar region of the wearer when the belt portion 101 is fastened around the wearer's waist. Preferably, the therapeutic packs 127 are sized so as to cover the wearer's entire back waist region when inserted into the slots, including the spinal cord and its surrounding muscles.

The pack support structure 125 are preferably formed from a single piece of waterproof and breathable material such as nylon, which is sufficiently strong to accommodate the weight of the pack without tearing, but which is thin enough so that the hot or cold effects of the packs can instantly be felt by the wearer. A mesh material, as shown, may be employed for the inner fabric of the support structures 125, or a piece of continuous material may be used.

As shown in FIG. 4, the inner fabric of the pack support structures 125 and the inner surface 123 of the belt portion 101 adjacent the therapeutic packs 127 have secured thereon strips of co-acting hook and loop fastening fabric 129, thereby allowing the wearer to close the openings formed by the pack support structures 125 and firmly position the gel packs 125 in the pack support structures. Other types of closure mechanisms, such snaps or buttons, may also be used to close the openings formed by the pack support structures.

A wide variety of therapeutic hot and cold packs are commercially available for use with the present invention. Ice packs, for example, are often distributed as pre-sealed plastic sacks containing refrigerant gels or liquids, but can also be homemade variants made from suitable plastic bags filled with crushed or cubed ice. Heat packs are also widely available as microwavable plastic sacks containing a liquid or a gel with a high specific heat. Commercially available electric heating and cooling packs may also be used.

As best shown in FIG. 5, the outer surface 131 of the rear portion 105 of the belt portion 101 is provided with one or more additional insert support structures 133 secured fixedly thereon and configured to removably receive one or more rigid inserts 135. Preferably, an insert support structure 133 is positioned in the belt portion 101 so that when worn, the inserts 135 each align spaced on each side adjacent the user's spinal cord so that the inserts 135, when placed in the insert support structures 133, provide additional support to the spinal cord and its surrounding muscles, or help the wearer maintain proper back alignment.

A user may choose not to use inserts 135 with the slots in pack support structures 133, since the inserts 135 further restrict the range of movement of the user's spine, potentially making it difficult for the wearer to engage in certain athletic, physical or everyday activities. This embodiment relying on the inserts may be desirable for individuals nursing a more serious back injury requiring extra support. The removable nature of the rigid inserts 135 means that the support garment can be selectively used with or without support, depending on the specific requirements of the selected activity of the user.

The inserts 135 are formed from a lightweight material, such as plastic or rubber, and have a variable resistance to bending that is determined by the insert's thickness and he properties of the material from which the insert 135 is formed. The inserts 135 are sufficiently thin so as to be less visible when the garment is worn under other clothing, and are of a sufficient length so as to extend over the lumbar region of the wearer extending above the pelvis. The insert support structures 133 receiving the inserts 135 are each preferably formed from a single piece of material having sufficient strength to accommodate the weight of the insert 135, and to secure the insert 135 in stiffening support of the belt portion 101.

Figure 6:
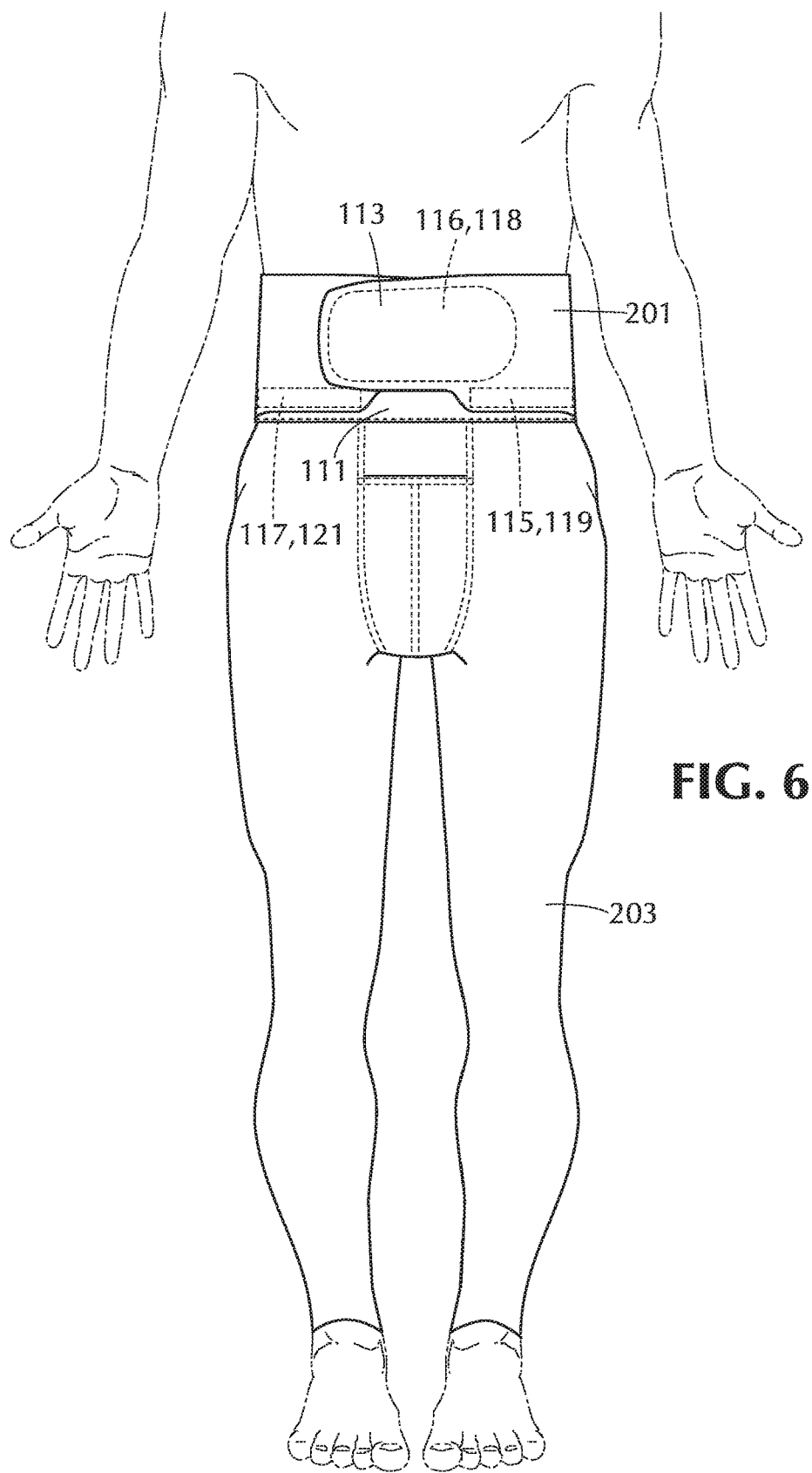
FIG. 6 is a front view of an alternate embodiment of the present invention as worn by a user.

In an alternate embodiment, which is depicted in FIG. 6, compression pants portion 203 extends downward past the wearers lower thigh, so as to also cover a user's knees and calves. This embodiment also provides added warmth and support to a wearer's calf muscles, and is preferable for wear during cold weather activities, such as skiing, skating, or snowmobiling. Belt portion 201 is configured similarly to the embodiment of FIGS. 1 to 5 and the same reference numbers are used for corresponding parts thereof.

Figure 7:
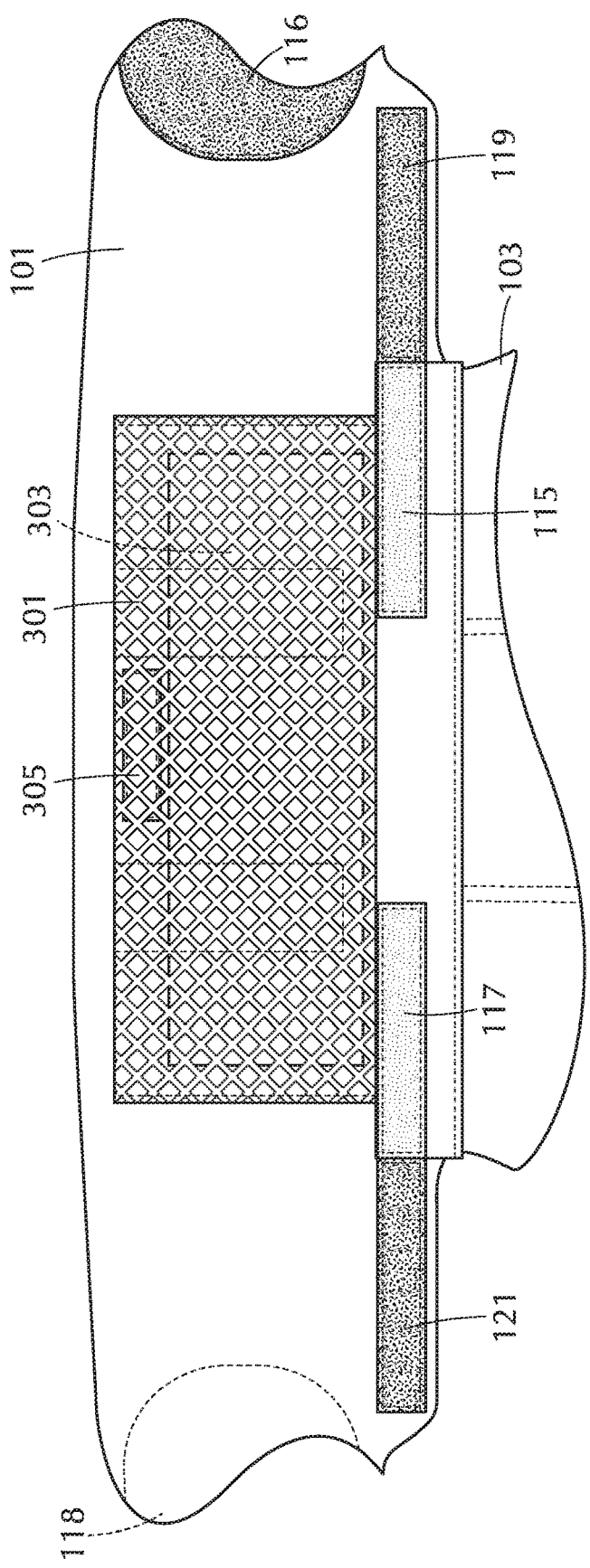
FIG. 7 is an enlarged partial front view of another alternate embodiment of the present invention, showing the showing the pack support structure having only one slot for receiving hot or cold packs.

In a further alternate embodiment of the invention, shown in FIG. 7, the pack support structure 301 has a single interior space extending laterally substantially across the back of the user. This structure 301 is configured to receive and support therein a single, elongated therapeutic hot or cold pack 303 that is sized so as to cover the wearer's entire back waist region in the interior space. The inner fabric of the pack support structure 301 and the inner surface 123 of the belt portion 101 adjacent the elongated hot or cold pack 303 are releasably severed to each other by strips of co-acting hook and loop fastening fabric 305 thereon, so as to allow the wearer to close the space 303.

The materials and construction of the belt 101 is otherwise similar to that of the belt portion 101 of the preferred embodiment, and similar reference characters are tested for complementary parts.

The back support garments described herein are usually designed to support rather than immobilize the wearer. The material is thin enough to make it breathable, yet it is flexible enough that it does not immobilize the wearer. It provides support to a wearer so that the wearer can avoid an injury and reduce or alleviate minor to moderate pain in the lumbosacral region of the wearer. In addition, the garment supports a wearer so the wearer can stay active and mobile for a longer period of time. The compression of the wearer by the belt in combination with hot or cold packs as described is in excess of 10 mmHg, which results in therapeutic levels of pressure.

Alternatively, in certain applications of the invention, needs of the wearer dictate a rigid immobilizing support of the wearer. This may be accomplished by providing rigid inserts in addition to the support, as will be described below.

Figure 8:
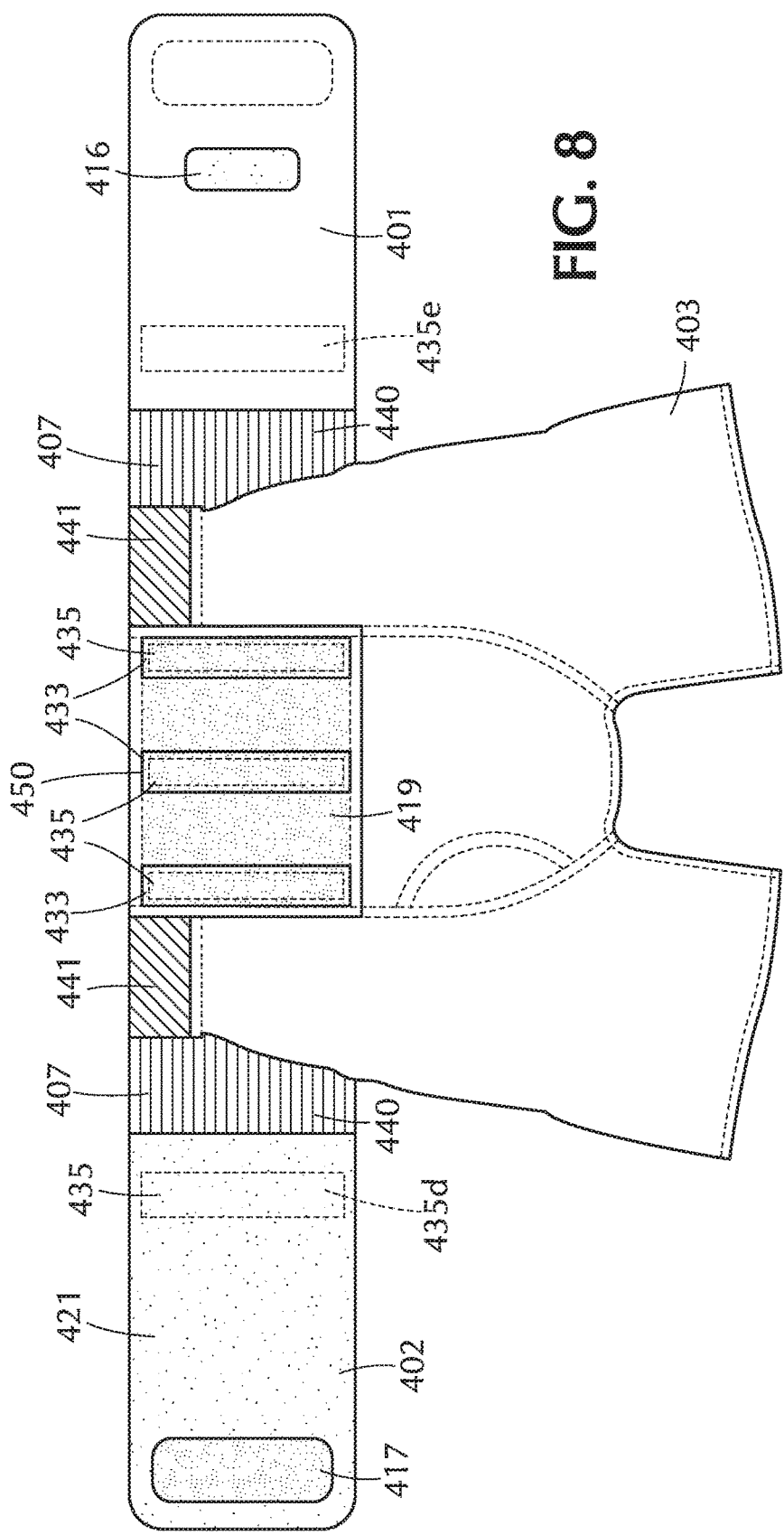
FIG. 8 is a front view of still another alternate embodiment of the garment.
Figure 9:
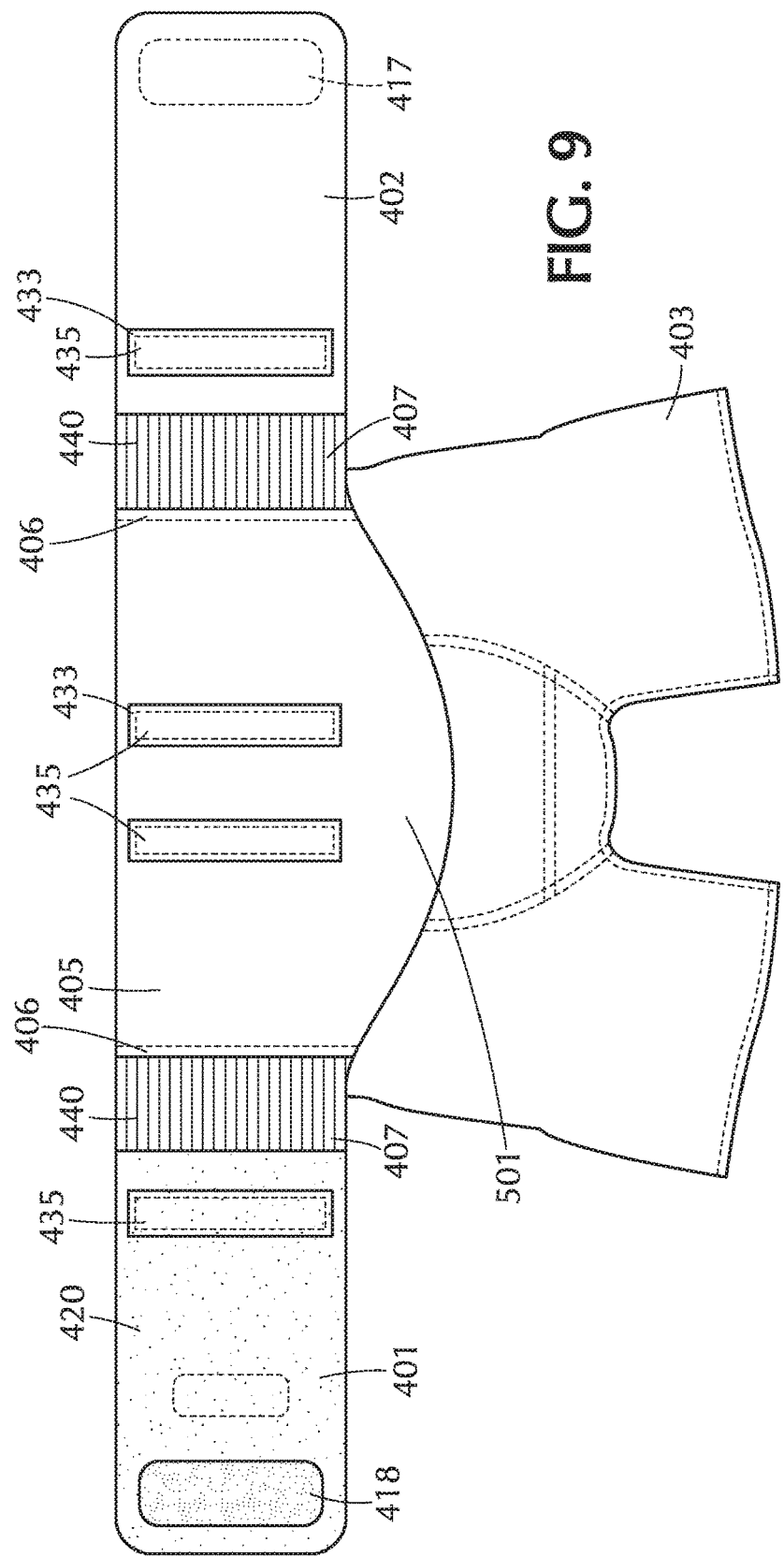
FIG. 9 is a rear view of the garment of FIG. 8.

Referring to FIGS. 8 and 9, another embodiment of the back support garment is configured to provide support to the lower back of a wearer. The garment includes compression pants 403 of elastic material, as described above, attached to a belt portion with left and right portions 401 and 402 extending laterally from a rear portion 405. The combination of a belt along with compression and hot or cold therapy is able to support the back and simultaneously provide maximum therapeutic support and maintain the therapy to a wearer throughout their physical, daily or athletic activity.

The system is capable of delivering affective heat therapy to the injury prone lumbosacral region of wearer. The heat therapy increases blood flow, which in turn decreases pain by dilating blood vessels and increasing blood supply to the targeted areas. Alternatively, cold therapy may also be applied to the lumbosacral region of a wearer, which reduces inflammation and decreases pain. The garment ultimately targets L4 and L5 of the lumbosacral spinal column so as to deliver and maintain therapy to an active user.

Referring to FIG. 9, the belt structure of the garment includes a center rear proton 405 of a relatively thick (e.g., 1.0 to 5.0 mm, $\frac{1}{16}$ inch or greater) elastic material that is rigidified by rigidifying structure in the form of vertically extending rib structures 435 that are fixedly attached, as by sewing, to the rear outward facing surface of the rear portion 405. The elastic material of the rear portion 445 is preferably an open cell foam laminated to a UBL (unbroken loop) material and a moisture wicking material on the other side. In the preferred embodiment, the material is Breathe-O-Prene™ by AccuMED.

The rear portion 405 of the belt specifically targets and supports lumbar vertebra four (L4) and lumbar vertebra five (L5) of the of the spinal column and also provides additional support 3.5 inches above and below L4/L5 extending upwards toward the thorax and downwards towards the sacrum. The rib structures 435 are positioned on the rear portion so as to overly the center of this area and to extend upwardly and downwardly therefrom.

Inserts 433 for the insert support structures 433 are preferably formed from metal spirals or "spiral" steel stays known in the area of supportive garments such as some reinforced brassieres or corsets. The spiral structure of the stays makes them relatively stiff against bending in one dimension, and relatively bendable in the perpendicular direction. These stays are removably inserted into a space between the sewn-on fabric part of the rib structure 435 and the material of the rear portion 405, with access given by a short interruption in the sewing securing the fabric, providing an opening adjacent the vertical end of the rib structure 435 communicating with the inside space. The vertical length of the rib is preferably between 4.5 and 6 inches, preferably about 5 inches.

The spiral stays provide support in both directions, meaning that they support a wearer while flexing medially and laterally, as well as in flexion and extension at the lumbosacral joint (between lumbar vertebra five and sacral vertebra one). The elastic material of the rear portion 405 in combination with the flexible stiffness of the stays cooperate to supply support to the user that provides comfort and support without immobilizing the user.

Because the stays are removable, a wearer may selectively insert more or fewer stays, or use more or less rigid stays, so as to adjust the amount of support. Alternatively, as mentioned previously, a user may need a rigidifying brace, and that may be accomplished by using very stiff stays, or more stays per rib structure 435, or the rear portion may be provided with a different design of pocket to receive a larger rigid plastic insert to produce a rigid support as will be described below.

The lateral end portions 406 of the rear portion 405 are each secured fixedly, as by stitching, to respective panels 440 of stretchable elastic material. The elastic material of panels 440 is thinner than that of the rear portion 405 or of left and right belt portions 401 and 402, which are fixedly attached and extend from opposite lateral ends 407 of panels 440 and are preferably of the same material as the rear portion 405, meaning, generally, material that is less elastic than that of panels 440, e.g., Breathe-O-Prene™. The elastic material of panels 440 is of a type described as woven power elastic, or other type of material that provides a lot of stretch and recovery, and it allows for a substantial amount of reversible stretching, so that the user can move, while the rear portion 405 maintains reinforcing support and pressure on the lower back area. The general feature here is that the panel is thinner, and able to stretch more with the wearer's movement. Comparable elastic material that is thinner than the material of the rear portion may be used. A large part of the total flexibility in terms of stretch of the belt portion of the garment comes from these panels 440.

Figure 10:
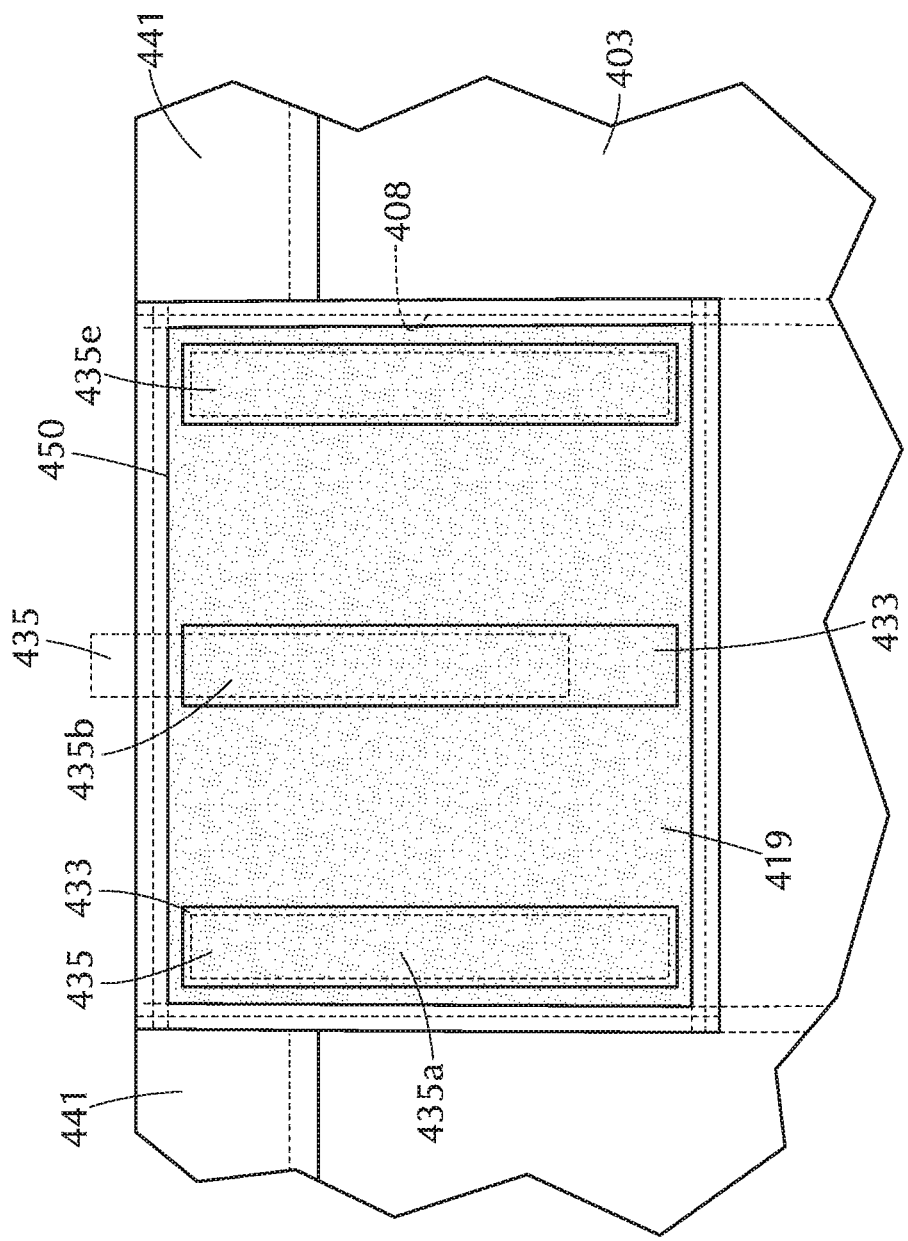
FIG. 10 is an enlarged detail view of the garment as shown in FIG. 8.

The front of the garment is also structured so as to provide support for the core of the user. As best seen in FIGS. 8 and 10, the upper portion of tie front of the pants 403 has a rectangular cut-out from its upper edge, in which a reinforcement panel 450 is secured by stitching. A horizontal strips or elastic band segment 441 is sewn to the upper edge of the shorts 403 with one end sewn to the rear portion and the other end to the edge of the front reinforcement or core stabilizer panel 450, and provide additional compression and support to the abdominal area of the wearer.

The core stabilizer panel 450 is of material similar to that of the rear portion of the belt, and it has thereon vertical reinforcement structures 435 configured similarly to the reinforcement structures 435 on the rear portion 405. Each has a respective reinforcement element or stay 433, preferably the flexible spiral type of stay as described above, removably inserted therein.

The core stabilizer panel 405 has a forward facing surface 419 that is the loop part of releasable hook and loop fastening material, e.g. VELCRO™ when worn, the wearer puts on the compression shorts 403 and then draws belt portion 401 across his midsection as tightly as desired, and hook-loop fastening material patch or area on belt part 401 is releasably secured to surface 419 of stabilizer panel 405. This leaves hook-loop fastening material area or patch 418 facing outward and forward on the front of to complementary surface 420 of the loop part of hook-loop fastening material.

Belt portion 402 is then drawn across the midsection of the wearer as tightly as desired. The belt portion 402 has a surface 421 that is the hooked part of hook-loop fastening material. The belt portion 401 and 402 are secured together with the hook portion 417 attaching releasably to the loop surface 420, and the hook portion 418 attaching releasably to the loop surface 421.

Figure 13:
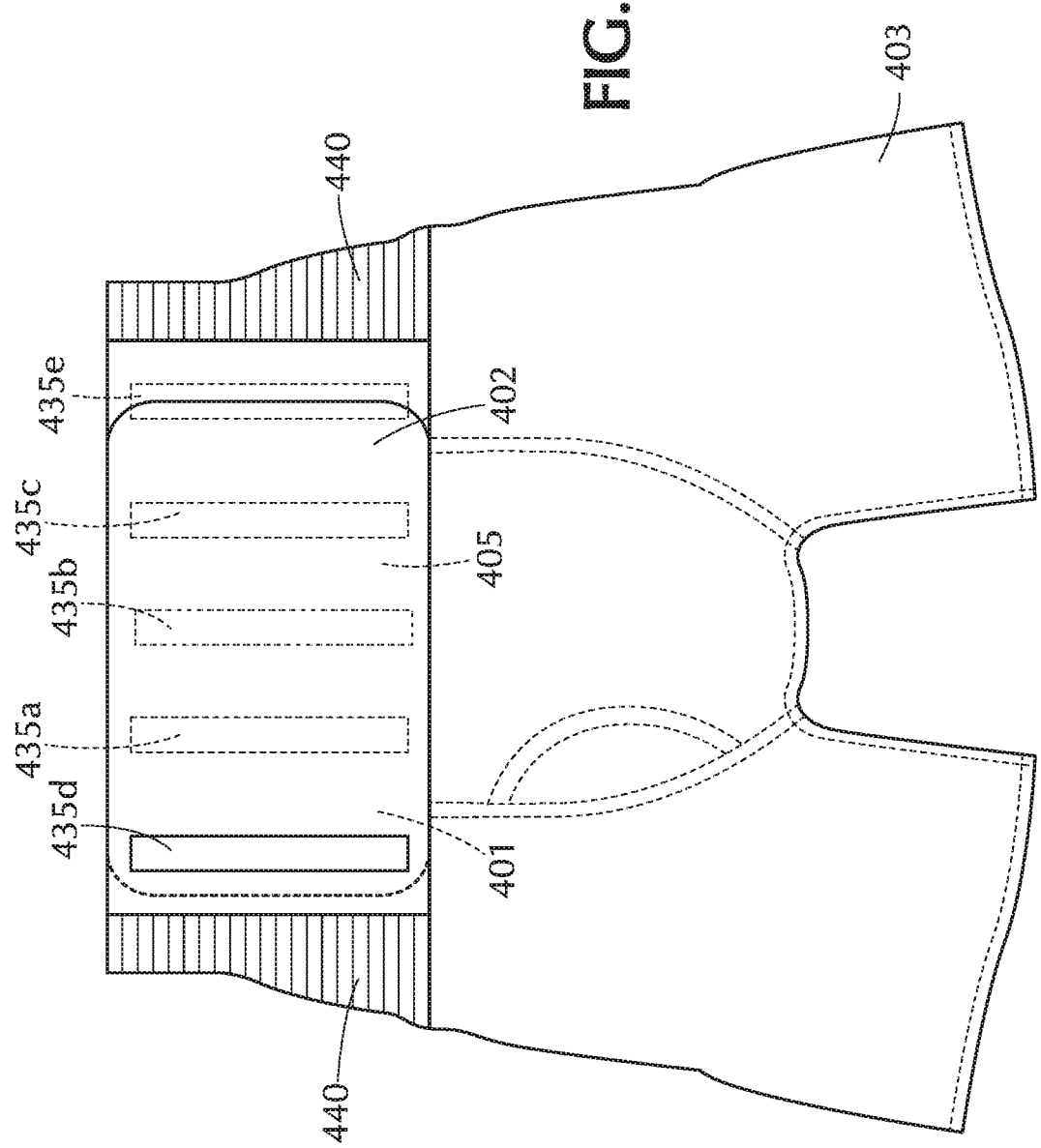
FIG. 13 is a front view of the garment of FIG. 8 on the body of a wearer.

The resulting assembly of the garment is best seen in FIG. 13. With belt parts 401 and 402 secured, the reinforcing ribs extend vertically and provide support of the abdomen core of the wearer. This results in five reinforcement rib structures, i.e., reinforcement structures 435a, 435b, and 435c on core stabilizer panel 405, reinforcement structure 435d on belt portion 402, and reinforcement structure 435e on belt portion 401.

In the embodiment shown, the core stabilizer panel 450 is configured to receive one or more additional insert support structures 433 for rigid inserts 435 that provide additional support to the abdominal muscles of the wearer. The core stabilizer panel 450 helps align the spine and provides additional support to the abdominal wall, which reduces pressure on the intervertebral discs located between adjacent vertebrae in the lumbosacral region.

In the embodiment shown in FIGS. 8, 9 and 10, the garment has seven insertable support structures 433, three in the abdominal region and two in the lumbar region of the back support 405 and one on each belt portion 401 and 402. Alternatively, the core stabilizer panel 405 may have an insertable rigidifying structure such as rigid plastic for additional abdominal support, as will be discussed below, when immobilization and not simply compression and support is desired.

Figure 11:
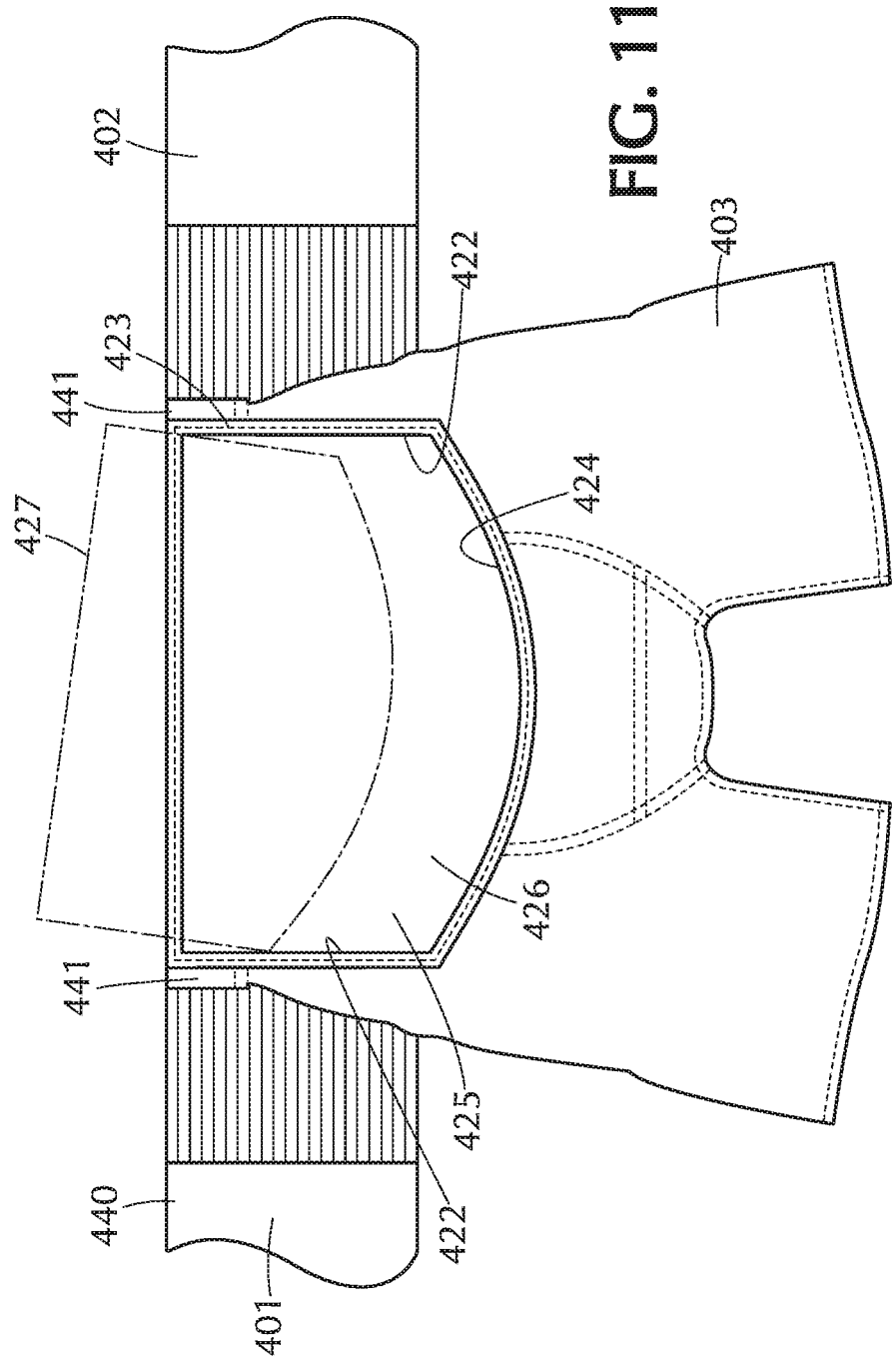
FIG. 11 is a rearward-looking sectional view of the garment showing the inside of the rear half of the garment.

Referring to FIGS. 9 and 11, the upper edge of the rear portion of the compression pants turns downward and runs across at a lower level and the back upward so that it defines a vertically-disposed cutout and the rear portion 405 of the belt is fixedly stitched or glued to the compression pants and extends upwards from the pants 403. The rear portion 405 of the belt is provided with a downwardly extending extra support portion 501 in the center of the rear portion 405, such that the rear portion 405 of the belt extends so as to effectively cover an area 3.5" above and below lumbar vertebra 4 (L4) and lumbar vertebra 5 (L5) of the lumbar region of the spinal cord.

As best shown in FIG. 11, the inner surface 423 of the rear portion 405 of the belt has a downward cutout from its upper edge that is generally rectangular, with vertical sides 422 and a downwardly curved lower edge 424 that generally follows the lower edge of the extension 501. A single layer of fabric 426 is sewn or otherwise secured to the side and bottom edges 422 and 424 of the cutout and to the rear portion 405, so that the fabric 426 lies over the cutout between the wearers body and the material of the rear portion 405, or more accurately, the fabric 426 is the innermost part of the rear portion 405 of the garment, and immediately outward thereof is the hot or cold pack.

The layer of the fabric is preferably mesh or thin fabric, and with the rear portion 405, defines an upwardly disposed hot or cold pack support structure 425 with one slot therein configured to receive a therapeutic hot or cold pack 427. The pack support structure 425 is positioned so as to maintain temperature transferring contact between the pack 427 and the body of the wearer through the sole intervening material of the inner fabric 426 of the pack support structure 425.

Figure 12:
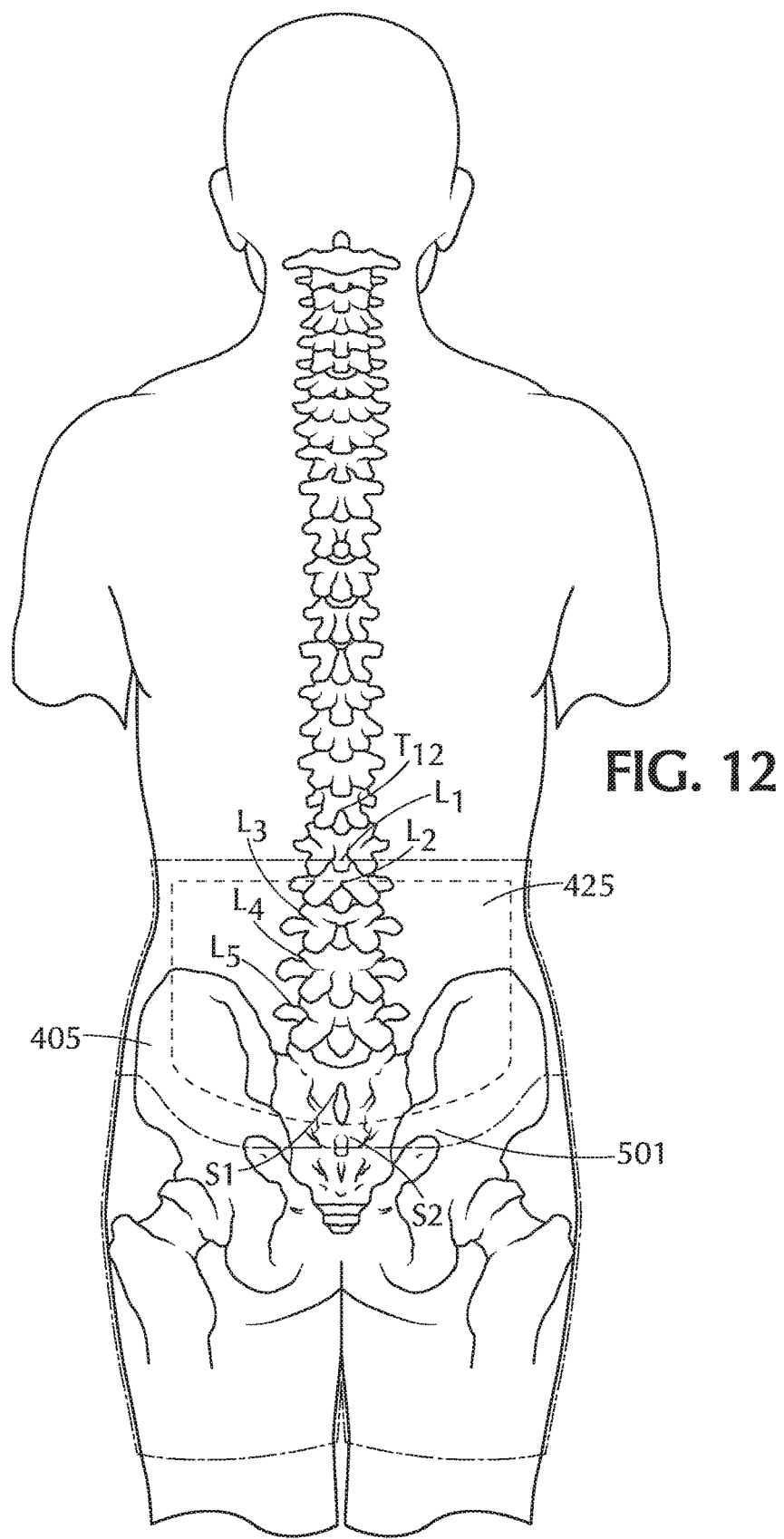
FIG. 12 is a schematic view of the garment of FIGS. 8 to 10, showing the location of a hot or cold pack thereof on the body of the wear.

The described combination of the compression shorts with the belt and hot or cold packs provides effective therapy to the lumbosacral region of the wearer. As shown in FIG. 12, when the back portion 405 is fastened around the wearer's waist the hot or cold pack 427 is positioned so that it overlies an area extending about 3.5 inches above and below the point midway between lumbar vertebra four (L4) and lumbar vertebra five (L5) of the wearer. Preferably, the therapeutic pack 427 when inserted into the pack support structure 425 is sized so as to cover the wearer's spinal column from approximately lumbar vertebral two (L2) and lumbar vertebra three (L3) to sacral vertebra two (S2) and sacral vertebra three (S3), including the lumbosacral joint (between lumbar vertebra five and sacral vertebra one) and the surrounding tissue lateral to the lumbosacral region. As shown in FIG. 12, the pack support structure also extends laterally so that most of the surrounding muscles of the lumbosacral region of the wearer are covered. In the embodiment shown, the pad is preferably approximately 8 to 9 inches wide.

The garment is a heat or cold therapy delivery device that is configured to bring those modalities to the wearer by compression engineered into the garment. The core support delivery system of the garment accentuates transfer of the hot or cold therapy because it is coupled with a therapeutic level of compression, above 10 mm of mercury pressure. The garment combination of compression pants, support belt and the hot or cold pack pocket with a single layer of fabric between the wearer and the pack keeps the hot or cold therapy located in the proper location in the lumbar region so as to provide maximum benefit, and it remains located appropriately in this location throughout physical, daily or athletic activity.

The combination of back or lumbar support with the abdominal support greatly increases the compression and greatly reduces pressure on the discs of the lower spine in the L4/L5 area. This area is where the rotation of the body takes place for almost all movement The garment produces a decrease in abdominal cavity pressure, which in turn decreases disc pressure in the lumbar region. The garment may reduce paraspinal activity and corresponding pressures on the discs and the lower back by as much as 19% or more. The provision of rigidifying structure, i.e., the stays in the abdominal or core support panel in combination with the stays in the lower back area improves and increases compression and provides better support, reducing pressure on the discs of the lumbar region of the wearer's spine. To be most effective for a wearer engaged in activity, the compression is centered on the L4/L5 region. Heat on the lumbar region loosens and relaxes to supporting muscles, e.g., the paraspinals and the obliques, and increases flexibility and range of motion, as well as reducing muscle spasms. The garment as described provides more consistent compression throughout the core of the wearer, and by so doing gives an improved range of motion.

The garment provides improved, stronger and more uniform compression throughout the garment. The abdominal support and docking structure provided in the front of the garment where the belt closing straps are secured to each other and to the body of the shorts is in the area where the greatest amount of compression takes place to stabilize the abdominals. The compression and support, and the hot or cold therapy application is in a position where the vertical midpoint of the affected area is at the joint between L4 and L5, and the area treated or compressed extends about 3.5 inches above and below the midpoint.

In addition, the support belt is breathable and capable of wicking moisture away from the wearer. The elastic side panels allow for especially improved comfort to the wearer, so as to not restrict breathing and provide freedom of movement to the wearer.

The hot and cold packs are preferably self-heating or self-cooling by chemical reactions therein, as well known in the art. Their shape conforms to the pocket in the back of the garment, i.e., a rectangular upper shape with a downwardly convex semicircular lower edge. The hot pack is configured so as to not heat up beyond a certain temperature so as to not give a burn to the wearer even if worn for an extended period, e.g., eight hours or more.

A garment of the invention may also be provided with a pouch on the inside surface of the front support panel that is configured to receive a hot pack for applying heat to the lower abdomen of the wearer. As with the hot or cold pack pouch in the rear portion of the garment, the pouch comprises a single layer of fabric or mesh material that constitutes the innermost surface of the garment, and the hot pack in the front of the garment is immediately forward of that layer. As a result, the hot pack is separated from the user only by the single layer of material, enhancing the flow of heat to the wearer.

Figure 14:
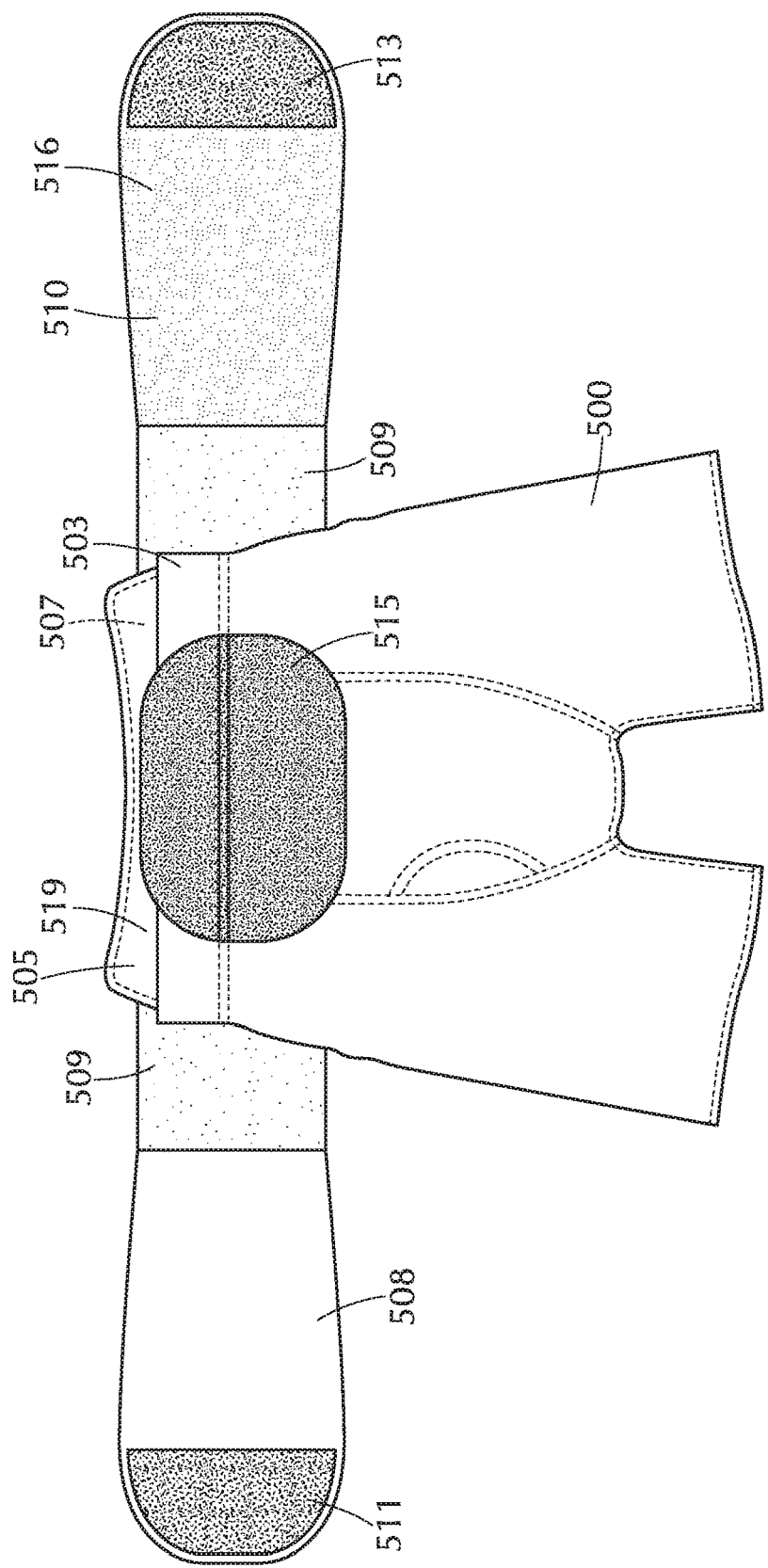
FIG. 14 is a front view another alternate embodiment of garment according to the invention.
Figure 16:
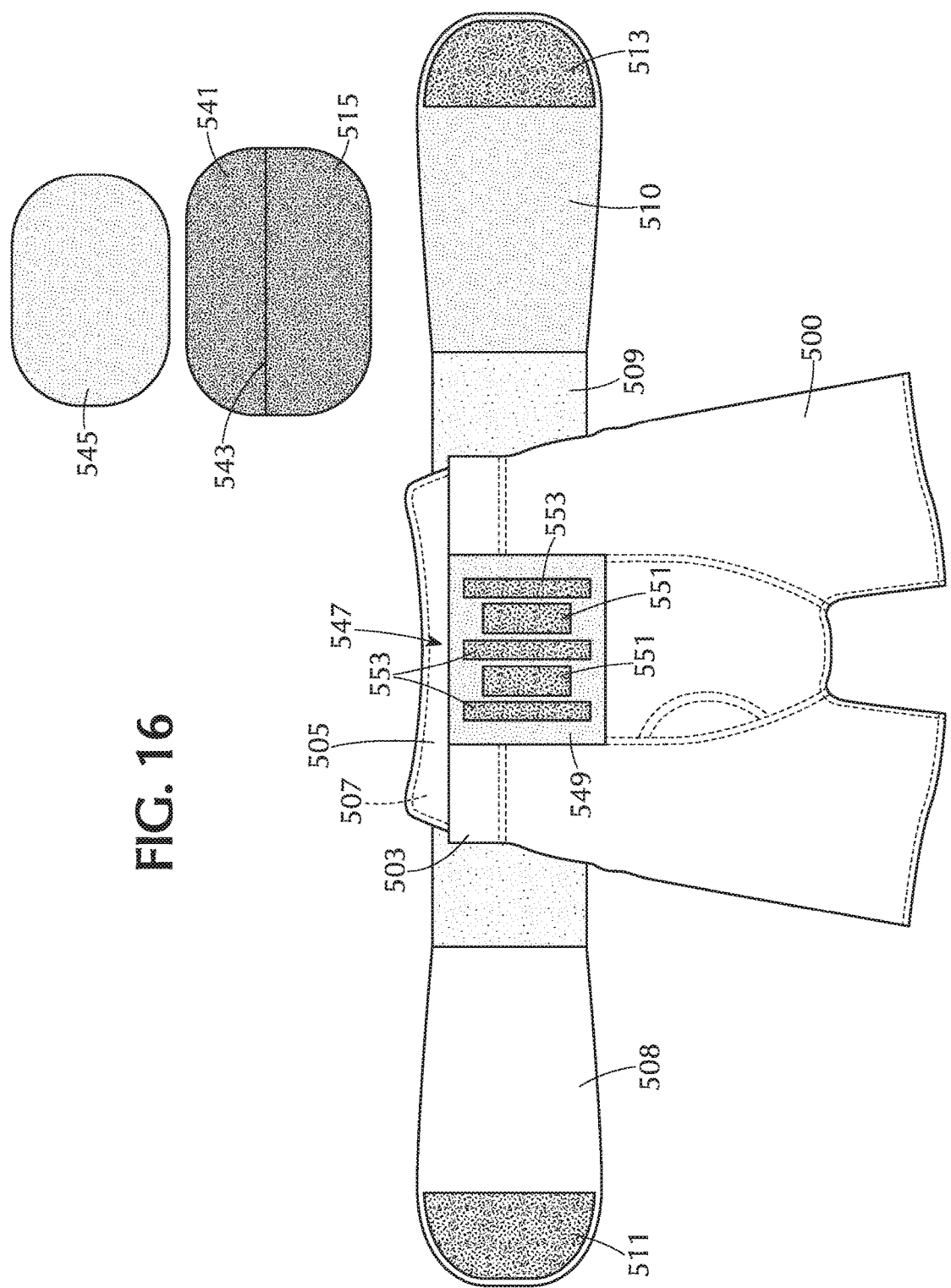
FIG. 16 is a that view of the garment of FIG. 14 with the rigidifying structure separated therefrom.

Referring to FIGS. 14 and 16, another alternate embodiment of garment is shown. The garment includes compression shorts 500 similar to those described above with respect to the previous embodiment, having a waistband 503. The shorts 500 are attached to a rear support portion 505, which contains a rigidifying member 507. The rigidifying member 507 is preferably a thermoplastic plate that is heated until pliable, then molded to a customized form that provides an appropriate contour for bracing the wearer's body, and then allowed to cool until rigid. Alternatively, the rigidifying member 507 may also pre-formed plastic that does not require heating.

The rear portion 505 is formed of relatively heavier elastic support material as discussed previously, and thinner-material elastic panels 509 are attached to and extend from the lateral ends of the rear portion 505. Belt securement portions 508 and 510 are formed of the same material as the rear portion 505, and are secured as by sewing to the distal ends of the panels 509. At least one side of the belt securement portion 510, the inward side, is UBL material configured to releasably attach to complementary hook material. Co-acting hook material portions 511, 513 and 514 are affixed to the belt securement portions 508 and 510.

Figure 15:
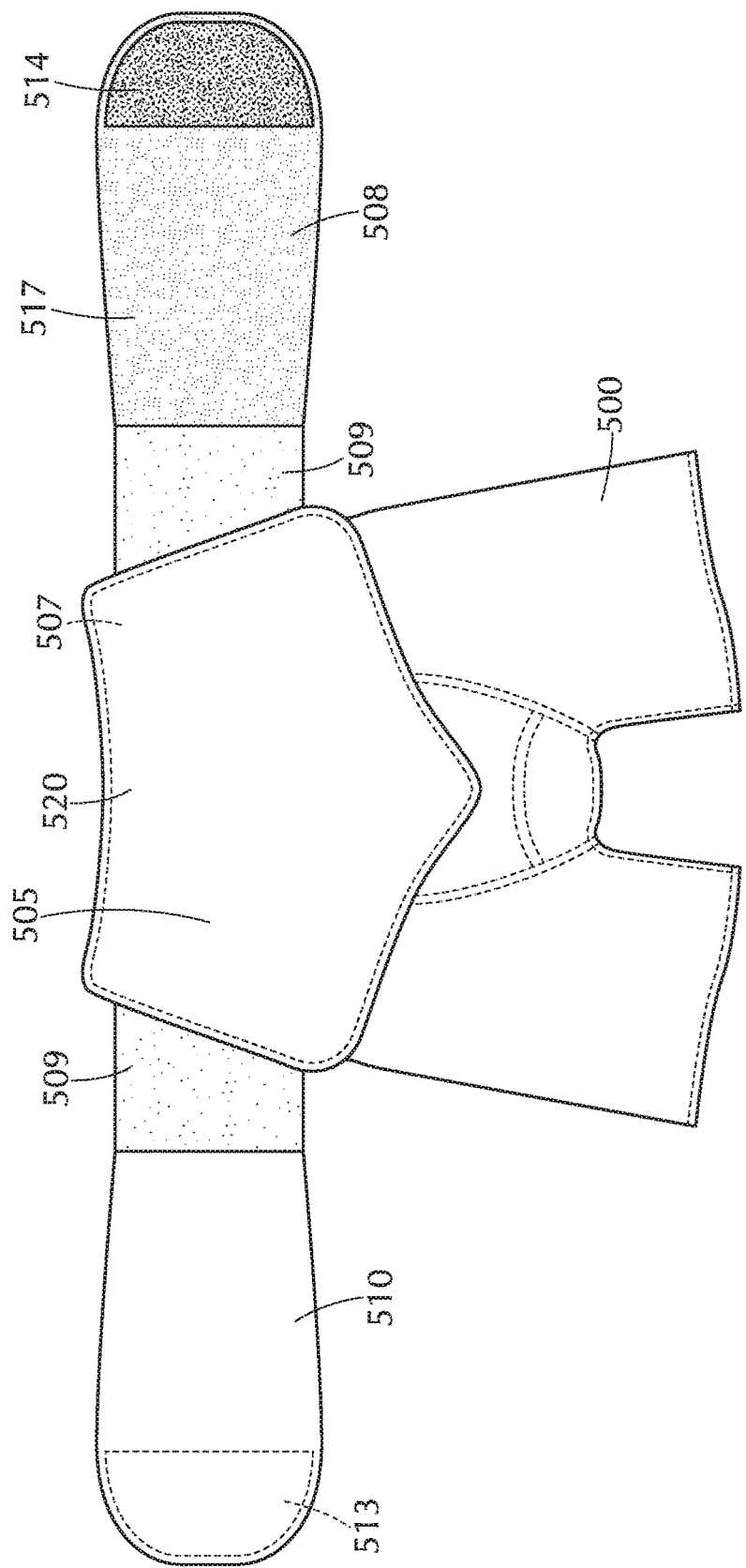
FIG 15 is a rear view of the garment of FIG. 14.

Rigidifying front structure 515 is releasably attached to the front of the shorts 500. Its outer surface is UBL material. The belt of the garment is secured so as to immobilize the wearer by drawing securement portion 508 until it firmly encircles the wearer, and then the associated hook material portion 511 is secured to the rigidifying structure 515. The other belt securement portion 510 is drawn across the waist of the wearer from the other side and the hook material patch 513 thereon is secured to the outward facing UBL surface 517 of the other belt securement portion, and the inward facing UBL surface 516 of belt securement portion 510 releasably attaches to hook surface portion 514, seen in FIG. 15. With the belt thus secured, the rigidity of the rear portion 505 and the rigidifying front structure 515 immobilizes the core of the wearer.

Figure 17:
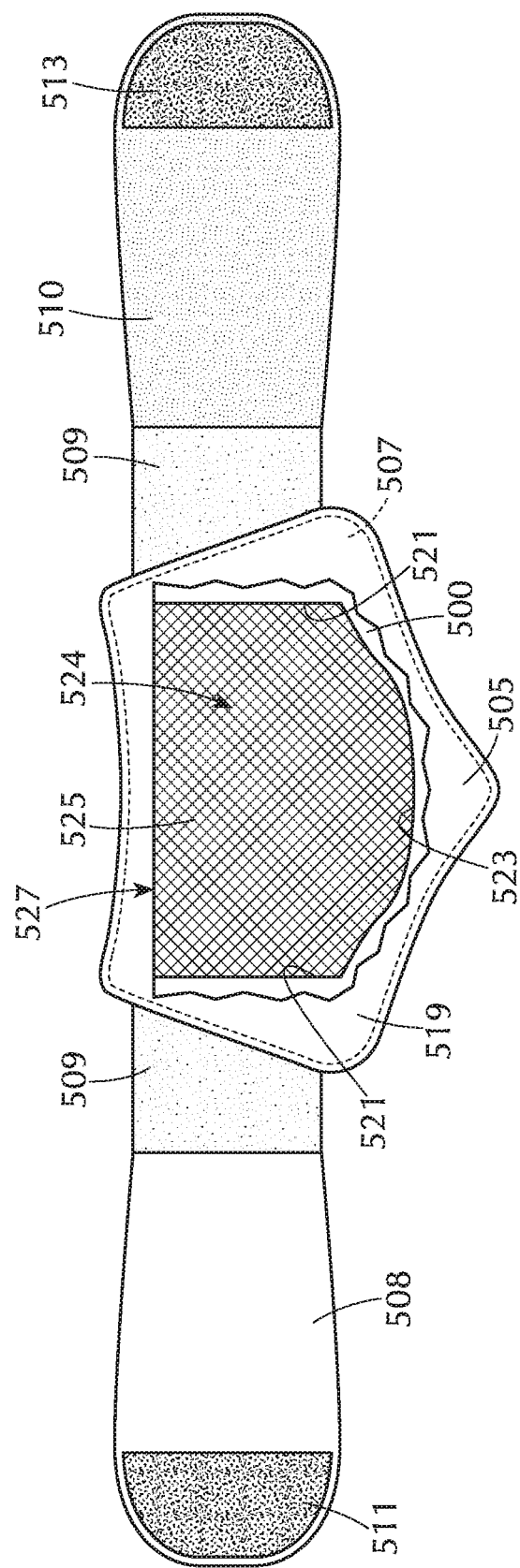
FIG. 17 is a rearward looking view of the belt portion of the garment of FIG. 14 with the shorts portion cut away.

The garment also provides for hot or cold pack application to the back of the wearer. FIG. 17 shows the structure of the rear portion 505 supporting the pack. The rear portion 505 is formed of an inward 519 and an outer piece 520 of the thicker support material sewn together so as to define a space therebetween receiving the rigid member 507. The inwardly facing surface of inward piece 519 is secured fixedly as by sewing to overly a cutout generally indicated at 524 defined by the upper edge of the shoe 500, which turns from horizontal to extend vertically downward along edges 521 and laterally across the curved bottom 523.

A corresponding shaped piece of fabric or mesh 525 overlies the cutout 524. It is also sewn to the sides 521 and the bottom edge 523, leaving a pouch with an open top edge 527 through which the hot or cold pack can be inserted to overly the back of the wearer with just the fabric or mesh 525 intervening.

Figure 18:
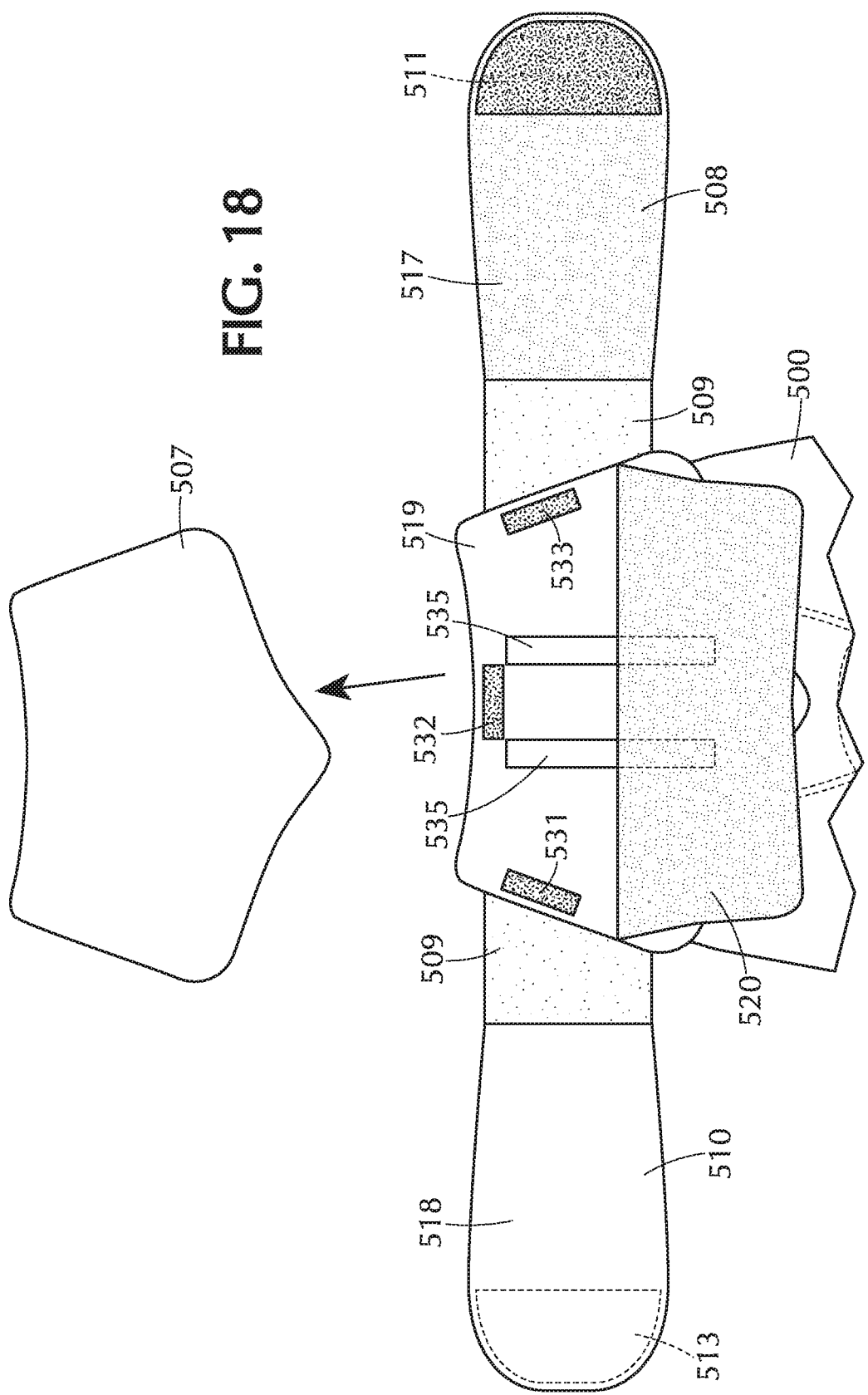
FIG. 18 is a rear view of the belt portion of the garment of FIG. 14 with the rigidifying structure removed.

The structure of the rear portion 305 is best shown in FIG. 18. Inward piece 519 and outward piece 520 are sewn together in a lower portion thereof, so as to snow the rigid member 507 to be inserted and withdrawn. When inserted the member 307 is secured in the space between pieces 519 and 520, with the space being secured by hook surface patches 531, 532, 533 affixed to the outward side of the inner piece 519. These patches 531, 532 and 533 releasably attach to the inward UBL surface of outer piece 520, securing the member 507 in the rear portion 505. Alternatively a zipper or some other form of closing system may be employed to secure the member 507 in the rear portion.

The rear portion 505 also has therein rigidifying structures 535 secured to the inner piece 519. These are preferably structures configured as described above, with stays of the spiral design described in the previous embodiment. These stays provide limited support for using the garment for support, not immobilization, if the wearer opts not to insert the rigid member 507.

The front rigidifying structure 515 and its support is more clearly disclosed in FIG. 16. Reinforcing structure 515 comprises an outer envelope 541 with a UBL material outer surface. The outer envelope is formed of two oval pieces of laminated elastic material with UBL surfaces outward sewn together around their perimeters so as to define therebetween an inner space sized to receive a rigid plastic plate 545. The outer envelope 541 has a slot 543 therein through which the rigid planar plastic plate 545 may be inserted into the interior space.

When so assembled the rigidifying structure is releasably attached to the central docking station indicated at 547. This docking station 547 is similar to the abdominal reinforcement structure of the previous embodiment. A rectangular pad 549 of UBL surface material is fixedly secured in a cutout in the front of the shorts 500, and it has secured thereto hook-surfaced patches 551. These patches 551 releasably secure the reinforcement structure 515 onto the front of the garment.

The central docking station is also provided with vertical reinforcement structures 553 similar to those described in regard to reinforcement structures 435a, 435b and 435c of FIG. 10, contain flexible inserts, such as spiral stays described above.

This design allows the wearer to omit the rigidifying structure 515, which is releasably secured to the docking station pads 551, and to also remove the rigid member 507 and use the garment providing more flexible support. The resulting non-immobilizing garment provides the flexible support similar to that described above with respect to the embodiment of FIG. 8. Support of the core of the wearer is provided by the flexible reinforcement structures 535 and 553, with support of the core at the abdomen and in the lumbosacral region of the wearer, generally an area extending equal distances upward and downward from the point midway between the LA and L5 vertebrae, covering from approximately S1 or S2 up to L2. In addition, further reinforcement may be added by providing one or more flexible insert reinforcement on belt portion 508 and 510 similar to reinforcements 435 in FIG. 8. In combination with the elastic portions 509, these reinforcements give core support to the wearer, while allowing the wearer to move more freely, as described in earlier embodiments, especially the garment of FIGS. 8 to 13.

It will be understood that the invention herein extends well beyond the embodiments of the disclosure, and the terms used in this specification should be understood to be language of description, not limitation, as those of skill in the art with this specification before them will be able to make changes and modifications therein without departing from the spirit of the invention.

What is claimed is:

1. A support garment for a wearer, said garment comprising:
   a compression pants portion being configured to provide support for the wearer's pelvis, legs, and groin area; and
   a belt portion attached fixedly to the compression pants portion and including a rear portion configured to align with, overlay, and support the lumbar region of the wearer when wearing the garment;
   the compression pants portion supporting thereon a core support structure configured to extend generally over the lower abdomen of the wearer when the wearer is wearing the garment;
   said core support structure including at least one reinforcement structure providing support for the abdomen of the wearer; and
   wherein the rear portion comprises a support portion of flexible elastic material having rigidifying structure, said support portion being configured such that the rigidifying structure of the support portion overlies and provides compressed support to a lumbosacral area of the wearer when wearing the garment irrespective of twisting or bending movement of the wearer, said supported lumbosacral area including L4 and L5 vertebrae of the wearer, and the support portion is configured such that the supported lumbosacral area extends substantially equal distances above and below a point midway between the L4 and L5 vertebrae; and
   said rigidifying structure and the support portion extending downward below said belt portion so as to overly and support at least a portion of the sacral area of the wearer.

2. The support garment according to claim 1, wherein the rear portion has vertically extending flexible reinforcement structures enhancing support thereof.

3. The support garment according to claim 2, wherein the belt portion includes belt securement portions each extending from a respective lateral side of the rear portion, one of said belt securement portions having an inward portion releasably securable to the core support portion or a front of the compression pants at a plurality of different positions, and an outward portion including part of a co-acting releasable securement structure, and the other of the belt securement portions having an inward facing portion with a complementary co-acting releasable securement structure allowing releasable securement to the outward portion of said one of said belt securement portions in a plurality of positions such that the wearer can adjust compression of the belt portion by selectively altering the position of releasable securement thereof.

4. The support garment according to claim 3, wherein the releasable securement is by co-acting hook surface material and unbroken loop material.

5. The support garment according to claim 3, wherein the belt securement portions support thereon reinforcement structures adjacent the core support structure when the belt portion is secured around the waist of the wearer.

6. The support garment according to claim 3, wherein the belt securement portions each include a respective panel of a second elastic material connecting with the rear portion, said second elastic material being easier to stretch than the elastic material of the rear portion.

7. The support garment according to claim 3, wherein said belt securement portions each has both hook and loop securement material surfaces facing complementary hook and loop surfaces on the opposing belt securement portion.

8. The support garment according to claim 2, wherein the rear portion is configured to support a rigid back member that immobilizes the wearer when so supported.

9. The support garment according to claim 8, wherein the core support structure includes a rigid front member that immobilizes a portion of the abdomen of the wearer.

10. The support garment according to claim 9, wherein the rigid front member is releasably secured to the core support structure so as to be removed by the wearer when not desired.

11. The support garment according to claim 10, wherein the rigid front member is releasably secured to the core support structure by co-acting hook and loop materials.

12. The support garment according to claim 2, wherein the rear portion has an inward surface facing the lumbosacral area comprised of fabric or mesh material that receives immediately rearward thereof a hot or cold pack, said hot or cold pack being configured to provide heat or cold treatment under compression of the belt to the lumbosacral area of the wearer through the fabric or mesh.

13. The support garment according to claim 12, wherein the compression pants have an upwardly disposed cutout therein around the hot or cold pack that is covered by the fabric or the mesh.

14. The support garment according to claim 1, wherein the core support portion is adapted to be laterally centered in front of the wearer when the wearer is wearing the garment and the rear portion is adapted to be laterally centered in back of the wearer when the wearer is wearing the garment.

15. The support garment according to claim 1, wherein the core support portion has flexible reinforcement members therein supporting the wearer's abdomen.

16. A support garment for a wearer, said garment comprising:
   a compression pants portion being configured to provide support for the wearer's pelvis, legs, and groin area; and
   a belt portion attached fixedly to and extending upwardly above the compression pants portion:
   said belt portion including a rear portion configured to overlay and support the lumbar region of the wearer;
   said belt portion being attached to said pants portion so as to align the rear portion with the lumbar region of the wearer;
   wherein the rear portion comprises a support portion of flexible elastic material configured such that the support portion overlies and supports a supported area of the wearer when wearing the garment and irrespective of twisting or bending movement of the wearer; and
   wherein the support portion of elastic material is configured such that the supported area over which the support portion overlies extends substantially equal distances above and below a point midway between the L4 and L5 vertebrae of the wearer; and
   wherein the belt portion includes first and second belt closing portions each attached to a respective lateral side of the rear portion, each of said belt closing portions extending from said rear portion to a respective belt end, said belt ends each having a respective co-acting belt securement portion, said belt securement portions being engageable with each other so as to secure the belt portion around the wearer and cause compression of the support portion onto the lumbosacral region of the wearer, and wherein the support portion is configured to extend downwardly below the belt closing portions and to overly at least a portion of the sacral area of the wearer when the support garment is worn by the wearer.

17. The support garment of claim 16, wherein the belt closing portions comprise first and second elastic portions each attached to the respective lateral sides of the rear portion, said elastic portions being of material that is thinner than the material of the rear portion.

18. The support garment of claim 17, wherein a core support portion is supported on a front of the compression pants located so as to overly the abdomen of the wearer when wearing the garment, the core support portion and the belt securement portions having coacting releasable securement structures such that one of the belt securement portions is releasably securable in a plurality' of positions to the core support portion such that tightness of the belt portion around the waist of the wearer may be selected, and the other of the belt securement portions being securable releasable over said one of the belt securement portions.

19. The support garment of claim 18, wherein the core support portion comprises a plurality of generally vertical reinforcement structures that support the abdomen of the wearer when wearing the garment.

20. The support garment of claim 19, wherein each belt securement structure has a reinforcement structure supported thereon contributing to support of the abdomen by the garment.

21. The support garment of claim 19, wherein the outer surface of said core support portion has insert-receiving structure supporting therein one or more inserts being configured to provide further support for the wearer's abdomen.

22. The support garment of claim 16, wherein the rear portion includes a layer of fabric between the support portion and the supported area of the wearer such that the layer of fabric forms a pouch configured to receive a hot or cold pack that, when inserted in said pouch overlies the L4 and L5 vertebrae of the wearer.

23. The support garment of claim 22, wherein the layer of fabric has an inward surface and an outward surface, wherein said inward surface constitutes a part of an interior surface of the garment, and the hot or cold pack when in the pocket engages the outward surface of the layer of fabric so as to transmit heat or cold to the wearer.

24. The support garment of claim 22, wherein the hot or cold pack, when inserted in said pouch, overlies a lumbosacral joint of the wearer and extends downward so that a heated or cooled area extends to at least the S1 or S2 vertebrae of the wearer and up to at least the L2 vertebra of the wearer.

25. The support garment of claim 22, wherein the compression pants portion has an upper edge that includes a downward cutout portion in front of the support portion, said layer of fabric being secured to the support portion so as to extend across said cutout.

26. The support garment of claim 16, wherein the support portion includes a rigid member that is configured to immobilize the wearer against some movements while the wearer is wearing the support garment.

27. The support garment of claim 26, wherein the rear portion has flexible reinforcement structures thereon so that the garment may be used for support when the rigid member is removed therefrom.

28. The support garment of claim 16, wherein the support portion is configured such that the support area extends down to at least the S1 vertebra of the wearer.

29. The support garment of claim 16, wherein the support portion of flexible elastic material configured has generally vertical rigidifying reinforcement members therein, said rigidifying members being spiral stays having differing bendability in different directions.

30. A support garment for a wearer, said garment comprising compression pants configured to provide support for the wearer's pelvis, legs, and groin area;

a rear portion of a first elastic material affixed to said compression pants so as to align with a lumbar region of the wearer's spine when the wearer wears the compression pants;

a pair of elastic segments of a second elastic material that stretches more easily than the first elastic material extending laterally from respective lateral sides of the rear portion;

a pair of belt closing portions connected to ends of the elastic segments distal to the rear portion;

the compression pants supporting on a forward abdominal portion thereof a core support structure having reinforcement structures therein configured to support a part of the abdomen of the wearer;

the belt closing portions having co-acting securement structures by which the belt closing portions are releasably secured to each other in front of the core support portion at selectable locations so as to provide selectable amounts of compression at the rear portion and the forward abdominal portion;

said rear portion having one or more vertically extending flexible reinforcement members and being configured to align with and support a lumbosacral region of the wearer centered on a midpoint between the L4 and L5 vertebrae of the wearer when the wearer is wearing the garment; and the rear portion having an innermost surface facing the lumbosacral region of the wearer, said innermost surface comprising a layer of fabric or mesh defining behind it a pouch configured to receive a hot or cold pack such that the hot or cold pack is separated from the innermost surface only by the layer of fabric or mesh, said hot or cold pack being sized to apply hot or cold treatment under compression to said lumbosacral area of the wearer;

whereby the wearer is provided with compression support of both the abdomen portion and lumbosacral area with hot or cold treatment applied to the lumbosacral area without movement thereof during activity of the wearer when wearing the garment.

31. The support garment according to claim 30, wherein the rear portion and the core support structure each has a respective removable rigidifying member operatively associated therewith, and when present, said rigidifying members immobilize the wearer against core movement.

32. The support garment according to claim 30, wherein the reinforcement structures and the reinforcement members comprise spiral stays each supported in a respective recess in the core support structure or the rear portion.

* * * * *